(12) United States Patent
Ginor

(10) Patent No.: US 7,302,292 B2
(45) Date of Patent: Nov. 27, 2007

(54) BREAST CANCER SCREENING

(75) Inventor: Ron Ginor, Austin, TX (US)

(73) Assignee: Mirabel Medical Ltd., Migdal HaEmek (IL)

( * ) Notice: Subject to any disclaimer, the term of this patent is extended or adjusted under 35 U.S.C. 154(b) by 201 days.

(21) Appl. No.: 10/510,025

(22) PCT Filed: Apr. 3, 2003

(86) PCT No.: PCT/IL03/00281

§ 371 (c)(1),
(2), (4) Date: Oct. 1, 2004

(87) PCT Pub. No.: WO03/084397

PCT Pub. Date: Oct. 16, 2003

(65) Prior Publication Data

US 2005/0065418 A1 Mar. 24, 2005

(51) Int. Cl.
*A61B 5/05* (2006.01)
(52) U.S. Cl. ............ 600/547; 600/507; 600/300; 600/587; 607/8
(58) Field of Classification Search .......... 600/547, 600/507, 300; 607/8
See application file for complete search history.

(56) References Cited

U.S. PATENT DOCUMENTS

| 3,608,543 | A | 9/1971 | Longini |
|---|---|---|---|
| 4,036,217 | A | 7/1977 | Ito et al. |
| 4,082,087 | A | 4/1978 | Howson |
| 4,291,708 | A | 9/1981 | Frei et al. |
| 4,328,809 | A | 5/1982 | Hirschowitz et al. |
| 4,387,721 | A | 6/1983 | Enjoji |
| 4,458,694 | A | 7/1984 | Sollish et al. |
| 4,493,039 | A | 1/1985 | Gregory |
| 4,510,939 | A | 4/1985 | Brenman et al. |
| 4,537,203 | A | 8/1985 | Machida |
| 4,539,640 | A | 9/1985 | Fry et al. |
| 4,617,939 | A | 10/1986 | Brown et al. |
| 4,763,660 | A | 8/1988 | Kroll et al. |
| 4,805,621 | A | 2/1989 | Heinze et al. |

(Continued)

FOREIGN PATENT DOCUMENTS

EP 0 050 353 10/1981

(Continued)

OTHER PUBLICATIONS

Kleinbaum, N. H.; "Dr. Ronny Ginor Saving Lives", published on <http://www.lifestylesmagazine.com>, 4 pages.

(Continued)

*Primary Examiner*—Max F. Hindenburg

(57) ABSTRACT

A method of screening for breast cancer, comprising: testing a plurality of asymptomatic women by measuring at least one electrical impedance characteristic on at least one breast, said asymptomatic woman being classified as belonging to a first group having a first risk factor for breast cancer; and re-classifying some of the women as belonging to a second group having a second risk factor greater than the first risk factor, based on the at least one impedance characteristic, wherein the second group has a risk factor of at least twice that of the first group, but less than 15 times that of the first group; and wherein fewer than 60% of those in the first group that have breast cancer are reclassified into the second group.

20 Claims, 8 Drawing Sheets

U.S. PATENT DOCUMENTS

| | | | |
|---|---|---|---|
| 4,819,658 | A | 4/1989 | Kolodner |
| 4,820,973 | A | 4/1989 | Alvarez |
| 4,823,797 | A | 4/1989 | Heinze et al. |
| 4,896,673 | A | 1/1990 | Rose et al. |
| 4,920,490 | A * | 4/1990 | Isaacson ................... 600/547 |
| 5,045,249 | A | 9/1991 | Jin et al. |
| 5,063,937 | A | 11/1991 | Ezenwa et al. |
| 5,070,862 | A | 12/1991 | Berlant |
| 5,099,846 | A | 3/1992 | Hardy |
| 5,143,079 | A | 9/1992 | Frei et al. |
| 5,178,147 | A | 1/1993 | Ophir et al. |
| 5,247,938 | A | 9/1993 | Silverstein et al. |
| 5,272,624 | A | 12/1993 | Gisser et al. |
| 5,282,840 | A | 2/1994 | Hudrlik |
| 5,295,483 | A | 3/1994 | Nowacki et al. |
| 5,353,802 | A | 10/1994 | Ollmar |
| 5,415,164 | A | 5/1995 | Faupel et al. |
| 5,454,377 | A | 10/1995 | Dzwonczyk et al. |
| 5,660,177 | A | 8/1997 | Faupel et al. |
| 5,715,821 | A | 2/1998 | Faupel |
| 5,749,369 | A | 5/1998 | Rabinovich et al. |
| 5,800,350 | A | 9/1998 | Coppleson et al. |
| 5,810,742 | A | 9/1998 | Pearlman |
| 6,026,323 | A | 2/2000 | Skladnev et al. |
| 6,122,544 | A | 9/2000 | Organ |
| 6,157,697 | A | 12/2000 | Mertelmeier et al. |
| 6,167,300 | A | 12/2000 | Cherepenin et al. |
| 6,179,786 | B1 | 1/2001 | Young |
| 6,179,790 | B1 | 1/2001 | Cundari et al. |
| 6,351,666 | B1 | 2/2002 | Cuzick et al. |
| 6,468,231 | B2 | 10/2002 | Sarvazyan et al. |
| 6,500,117 | B1 | 12/2002 | Hancock |
| 6,768,921 | B2 | 7/2004 | Organ et al. |
| 6,952,606 | B2 * | 10/2005 | Anderson et al. ........... 600/547 |
| 2001/0051774 | A1 | 12/2001 | Littrup et al. |
| 2002/0123694 | A1 | 9/2002 | Organ et al. |
| 2002/0183645 | A1* | 12/2002 | Nachaliel ................... 600/547 |
| 2003/0078482 | A1 | 4/2003 | Kenan et al. |
| 2003/0078510 | A1 | 4/2003 | Olson et al. |

FOREIGN PATENT DOCUMENTS

| | | |
|---|---|---|
| EP | 0 190 043 | 8/1986 |
| GB | 2 138 148 | 10/1984 |
| GB | 2 273 987 | 7/1994 |
| GB | 2 276 326 | 9/1994 |
| WO | WO 91/13584 | 9/1991 |
| WO | WO 93/23112 | 11/1993 |
| WO | WO 94/20012 | 9/1994 |
| WO | WO 96/12439 | 5/1996 |
| WO | WO 01/43630 | 6/2001 |
| WO | WO 01/64102 | 9/2001 |

OTHER PUBLICATIONS

Anah, J. et al.; "Multi-Function Interface Unit for Applied Potential Tomography;" Nov. 1998; pp. 287-288; Proceedings of the Annual International Conference of the IEEE Engineering in Medicine and Biology Society (IEEE Cat. No. 88CH2566-8); XP002171794.

Piperno, G. et al.; "Breast Electrical Impedance and Estrogen Use in Postmenopausal Women"; Year 2002; Maturitas: The European Menopause Journal; 41; pp. 17-22.

Masuda et al.; "Topographical Map of Innervation Zones within Single Motor Units Measured with a Grid Surface Electrode"; Aug. 1988; pp. 623-628; IEEE Transactions on Biomedical Engineering; vol. 35; No. 8; XP000005699; New York, US.

Monster et al.; "A System for the Rapid Acqisition of Surface Potential Maps of Human Skeletal Muscle Motor Units;" Feb. 2, 1980; pp. 110-112; IEEE Transactions on Biomedical Engineering; vol. 27; No. 2; XP002114215; New York, US.

Riu et al.; "In Vivo Static Imaging for the Reactive Parts in Electrical Impedance Tomography Using Multifrequency Techniques;" Oct. 1992; pp. 1706-1707; Proceedings of the Annual International Conference of the Engineering in Medicine and Biology Society; vol. 5; No. 14; XP000514393; US.

Cespedes et al.; "Elastography: Elastic Imaging Using Ultrasound with Application to Muscle and Breast in Vivo;" Apr. 1993; pp. 73-88; Ultrasonic Imaging; vol. 15; No. 2; XP000383142; Orlando, US.

Eyuboglu et al.; "In Vivo Imaging of Cardiac Related Impedance Changes; " Mar. 1989; pp. 39-45; IEEE Engineering in Medicine and Biology; vol. 8; No. 1; XP000002279; New York, US.

Record et al.; "Multifrequency Electrical Impedance Tomography; " Jul. 1992; pp. 47-50; Clinical Physics and Physiological Measurement, Suplement A; vol. 13; XP000431598; York, GB.

Zhili Huang, et al.; "Bioimpedance Measurement: Theory, Experiment and Application;" Nov. 1987; pp. 1416-1427; Proceedings of the Ninth Annual Conference of the IEEE Engineering in Medicine and Biology Society; vol. 3; XP000015434.

Piperno, G. et al.; "Breast Cancer Screening by Impedance Measurements;" 1990; pp. 111-117; Frontiers Med. Biol.; vol. 2.

Esselle, et al.; "Capacitive Sensors for In-Vivo Measurements of the Dielectric Properties of Biological Materials;" Mar. 1988; pp. 101, 104-105; IEEE Transactions on Instrumentation & Measurement; vol. 37; No. 1.

Gersing, E.; "Messung der Elecktrischen Impedance von Organen-Apparative Ausrustung fur Forschung und Klinishe Anwendung;" 1991; pp. 6-11; Bimed. Technik 36; (including abstract in English).

Vrana, J. et al.; "Mesure de L'Impedance des Tissus Hepatiqueles Transforms pas des Processus Lesionels;" 1992; pp. 165-168; Ann. Gastoentreaol. Hepetol.; vol.28; No. 4; (including abstract in English).

Rajshekhar, V.; "Continuous Impedance Monitoring During CT-Guided Stereotactic Surgery: Relative Value in Cystic and Solid Lesions; 1992; pp. 439-444" British Journal of Neurosurgery (1992); vol. 6.

Mastrototaro, J.J. et al.; "Rigid and Flexible Thin-Film Multi-Electrode Arrays for Transmural Cardiac Recording;" Mar. 1992; pp. 271-279; IEEE Trans. Biomed. Engr.; vol. 39, No. 3.

Buckles, D. S. et al.; "Image-Base Display of Activation Patterns Derived from Scattered Electrodes;" IEEE Trans. Biomed. Engr.; vol. 42; No. 1; Jan. 1995; pp. 111-115.

Smith, R. W. M. et al.; "A Real-Time Electrical Impedance Tomography System for Clinical Use-Design and Preliminary Results;" Feb. 1995; pp. 133-139; IEEE Trans. Biomed. Eng.; vol. 42.

Surowiec, A. J. et al.; "Dielectric Properties of Breast Carcinoma and the Surrounding Tissues;" Apr. 1988; pp. 257-263; IEEE Trans. Biomed. Eng.; vol. 35; No. 4.

Heimbach, M.; "Measures of Performance; " 1990; pp. 158-174; Electrical Impedance Tomography; (12.1).

Davies, R. J. et al.; "Detection of the Cancer-Prone Colon, Using Transepothelial Impedance Analysis;" Apr. 1989; pp. 480-484; Arch Surg.; vol. 124.

Morimoto, T. et al.; "A Study of the Electrical Bio-Impedance of Tumors;" 1993; pp. 25-32; Journal of Investigative Surgery; vol. 6.

Man et al.; "Results of Pre-Clinical Test for Breast Cancer Detection by Dielectric Measurements;" Aug. 12-24, 1979; International Conference of Medical and Biological Engineering, V International Conference of Medical Physics; 30.4; Jerusalem, Israel.

Riu, P. et al.; "A Broadband System for Multifrequency Static Imaging in Electrical Impedance Tomography"; 1992; pp. 61-65; Clin. Physiol. Meas.; vol. 13; Suppl. A.

Rigaud, B. et al.; "Experimental Acquisition System for Impedance Tomography with Active Electrode Approach; " Nov. 1, 1993; pp. 593-599; Medical and Biological Engineering and Computing; vol. 31; No. 6; XP000415771.

Korte, C.J.; "Subsurface Electrical Impedance Imaging Using Orthogonal Linear Electrode arrays;" Jan. 16, 1996; pp. 41-46; IEEE Proceedings: Science, Measurement and Technology; vol. 143; No. 1; XP006006750.

TransScan Medical Inc.; "TransScan Medical Announces Initial Closing of $2.5 Million as Part of Larger Financing Round"; News Release, Oct. 2002, 2 pages.

TransScan Medical Inc.; "New Technology for Breast Cancer Detection in Young Women Featured ar Emerging Medical Technology Conference"; News Release, Oct. 2002, 1 page.

TransScan Medical Inc.; "A New Modality for Early Detection of Breast Cancer in Young Women"; Company Fact Sheet, 3 pages.

TransScan Medical Inc.; "Breast Cancer, Young Women"; Corporate Profile, Oct. 2002, 1 page.

* cited by examiner

BREAST CANCER SCREENING

RELATED APPLICATION

The present application is a U.S. national application of PCT Application No. PCT/IL03/00281, filed on Apr. 3, 2003.

FIELD OF THE INVENTION

The present invention relates to systems for tissue characterization and particularly for detecting breast cancer.

BACKGROUND OF THE INVENTION

Breast cancer is a major cause of mortality in women. One of the factors that influence the chances of curing a patient having breast cancer is early detection of the disease. The major methods for detecting breast cancer currently in use are X-ray mammography imaging and ultrasound imaging. In detecting breast cancer, an image of the breast is generated, using one of these imaging modalities, and a physician inspects the image to determine whether the image is indicative of breast cancer. Such inspection of images requires image analysis specialization from the physician, which adds to the cost of the cancer detecting procedure and/or limits the availability of the procedure to relatively large medical centers. Therefore, in general, only women in high risk groups of breast cancer undergo tests for early detection of breast cancer. These risk groups include, for example, women above the age of about 45 and women having a family history of breast cancer. Generally, different countries set different ages in which X-ray mammography screening is recommended. The chances that a woman in a risk group has cancer is usually much less than 10% and therefore even many women in the risk groups do not go for regular breast cancer detection procedures as recommended.

For women not in a high risk group, for example in the age group of 25-45, there are very low chances, in accordance with current practice, that their cancer will be detected at an early stage. These women, however, have a chance of about 3 to 1000 of having breast cancer, which may not be detected until the cancer is in advanced stages. Women's physicians and aware women perform palpation tests in search for cancer and woman who have suspected lumps detected in their breasts by palpation are sent for further screening by ultrasound and/or mammography and/or biopsy. However, due to the low risk within the general population, mammography and/or ultrasound are not indicated as screening tools for the general asymptomatic population.

U.S. Pat. No. 5,800,350, to Coppleson et al., the disclosure of which is incorporated herein by reference, describes a probe adapted to apply a plurality of stimuli to a suspected tissue. According to detected responses to the stimuli, the probe provides an indication of the surface tissue type (e.g., normal, pre-cancerous/cancerous, unknown) of the suspected tissue. The probe of U.S. Pat. No. 5,800,350 is not suitable for use with the breast, as cancerous cells in the breast are not generally on the surface of the breast.

An article titled "Breast Electrical Impedance and Estrogen Use in Postmenopausal Women", G. Piperno, S. Lenington, Mauturitas 41 (2002), the disclosure of which is incorporated herein by reference, describes a clinical test which suggests a correlation between electrical measurements on the nipple and estrogen activity in breast tissue.

U.S. Pat. No. 6,122,544 to Organ, the disclosure of which is incorporated herein by reference, describes a method of identifying cancer by comparing maps of electrical impedance measurements of the breasts. The impedance maps (in the form of matrices) of both breasts of the patient are compared and if a substantial difference is found, cancer is diagnosed in the breast with the higher impedance. U.S. patent publication 2002/0123694 to Organ et al., the disclosure of which is incorporated herein by reference, uses a greater number of electrodes and attempts to localize the lesion, according to a region of the map having a different impedance.

U.S. Pat. No. 5,415,164 to Faupel, the disclosure of which is incorporated herein by reference, describes a self-test method for a breast screening system based on measurement of passive DC signals from the breast. As DC signals require long settling times (due to polarization) before measurements may be acquired, the method includes determining whether the measured signals are stable before measurement of the DC signals for breast screening is allowed, so that it is not required to wait long periods of time when it is not necessary. Such stabilizing waiting periods are characteristic of DC measurements, especially in polarizable materials.

U.S. Pat. No. 6,167,300 to Cherepenin, the disclosure of which is incorporated herein by reference, describes an electric mammography system for obtaining three dimensional images of the breast. The system uses a large surface probe, which may include elements that do not contact the examined breast. These elements are detected according to the values they sense and are excluded from the reconstruction of the three dimensional image.

U.S. Pat. No. 6,026,323 to Skaldnev, the disclosure of which is incorporated herein by reference, describes a probe for characterizing tissue type, for example for breast cancer examination. The probe checks for poor contact due to reasons such as the probe being in an angle to the cervix.

The use of impedance measurements in screening has been mooted by several authors. However, no such screening method has ever been shown to be feasible. In particular, screening requires both high specificity and high sensitivity. In general, it was believed that in the absence of both high sensitivity and specificity, if screening was performed on a general population in which the probability of cancer of the breast is low, either large numbers of women would be subjected to unnecessary additional tests or many woman with cancer would be diagnosed as being free of cancer. It should be noted that mammography, which is used for testing high risk groups has a high sensitivity but a low specificity as do other modalities used to "screen" suspect patients.

SUMMARY OF THE INVENTION

In the past, attempts have been made to provide a definitive or semi-definitive diagnosis for breast cancer based on impedance measurement. In general, these attempts have failed since they require that the results have both a high specificity and a high sensitivity. Unfortunately, impedance imaging methods to date have not been able to provide such a combination. Impedance imaging has provided a useful adjunct to conventional diagnostic methods such as mammography and ultrasound imaging, in which case it can be effective when configured in a high sensitivity, low specificity mode.

Attempts have been made to utilize impedance imaging as a scanning tool. To be effective, again, high sensitivity and specificity are necessary, since false positives result in unnecessary and sometimes dangerous situations and false negatives can be deadly.

In an aspect of some embodiments of the invention, impedance imaging is used in a relatively high specificity, relatively low sensitivity mode. Generally such screening is not considered effective, since it means that large numbers of false negative indications are provided. However, for some classes of examinees, such methods can be effective.

In an embodiment of the invention, low risk groups, such as pre-menopausal women between the ages of 20 and 45, or 25–40, for whom standard screening is not considered justified, are tested using impedance techniques. In this group, the occurrence of breast cancer is less than about 3–4 in 1000. This group is thus not a candidate for normal mammographic screening, except when there are significant risk factors, such as having close relatives with breast cancer. Having two first degree relatives with cancer, which warrants early mammography breast cancer screening, raises the probability to have cancer by a factor of 2.9 to about 8.7 in 1000. Diagnosis of atypical hyperplasia raises the probability by a factor of having cancer to about 12 in 1000 and women identified as carrying a BRCA gene are considered to have a cancer risk of about 17 in 1000.

However, utilizing a method of the present invention (or some prior art methods with suitable thresholds), a smaller group can be chosen from the general population with a higher risk, estimated to be as high as 11–20 in 1000.

Unlike other screening procedures, which attempt to find patients who have the disease with relatively high certainty, the present methodology is used to choose a higher risk group out of a lower risk group, which will then be screened using more definitive screening.

An aspect of some embodiments of the present invention relates to a method of identifying groups of women with high risk for breast cancer. The method includes comparing values of one or more dielectric parameters determined from signals measured from tested women to values of those parameters from a learning group of women with and without cancer. According to the comparison, an indication is made as to whether the tested women belong to a high risk group for breast cancer, the women in the high risk group having no more than a 2–5% chance for having cancer. Stated otherwise, women in the high risk group have a cancer probability 4–10 times greater than asymptomatic women (i.e., a risk factor of 4–10). The identification of women as belonging to a high risk group, rather than as either having or not having cancer symptoms, allows applying tests to selected portions of the general low risk population who otherwise would not be examined at all, thus finding a larger percentage of cancerous women.

In some embodiments of the invention, impedance tests of the present invention are applied to women in low risk groups who generally are not instructed to perform screening using other modalities. Optionally, the impedance tests are performed on asymptomatic women who have no symptoms requiring additional testing for breast cancer. Optionally, the impedance tests are performed on pre-menopausal women and/or women who do not use hormones, as it has been found that on these groups of women a higher specificity was achieved. Alternatively or additionally, the impedance tests are performed on young women (e.g., up to age 40–45), for example in the age group of 25–40, as the specificity and sensitivity of impedance tests decrease with age, but the probability of cancer increases with age. In an exemplary embodiment of the invention, tests are performed on a smaller age group, for example between 35–45. In some embodiments of the invention, the impedance tests do not search for a lesion, but rather search for general impedance characteristics of a malignant breast.

An aspect of some embodiments of the invention relates to methods and apparatus for breast screening. In the past, methods utilizing impedance attempted to determine the location of a lesion or at least based their determination on methods that depended on the location of the lesion. This is the basis for most of the breast imaging methodologies described above.

The present aspect is radically different in that it does not attempt to determine the site of a cancer, but rather gives a risk score, which is indicative of whether a cancer is present in a particular breast tested or in an (optionally) unstated one of a pair of breasts. Thus, in some embodiments, the score is a global score that does not even indicate which breast is involved.

This aspect of the invention is made possible by the discovery of methods that indicate the presence of breast cancer, using impedance measurements, without utilizing image analysis or array manipulation of data representing the volume of the breast in the determination.

An aspect of some embodiments of the present invention relates to providing an indication of the chances of a patient having breast cancer, at least partially based on a dielectric parameter of a nipple region of the breast. The term nipple refers herein to the area including both the nipple tip and the areola.

One theory as to why a measurement in the nipple region has been found to serve as a relatively good cancer predictor is that breast cancer often develops in early stages in the ducts of the nipple. By determining whether a breast includes abnormal impedance values in the area of the nipple (and in some embodiments, limited to the areola surrounding the tip of the nipple), a useful indication of whether the breast includes cancerous or pre-cancerous tissue can be made available. In addition, the low impedance of the areola allows for a good "window" into the breast. Therefore, signals sensed at the nipple can provide an indication for the entire breast.

An aspect of some embodiments of the present invention relates to providing an indication of the chances of an asymptomatic patient having breast cancer, based on one or more local impedance measurements from one or more breasts of the patient. The local impedance measurements are used to determine a dielectric parameter representative of the entire breast or of the patient, under the understanding that many breast cancer cases affect the impedance of the entire breast and not only of a local region in which a tumor develops.

In some embodiments of the invention, in order to allow fast screening, the local impedance measurements are acquired in a limited number of positions of a probe on the breast, optionally in only a single positioning. In an exemplary embodiment of the invention, a small probe, covering less than 20%, or even less than 15% of the breast is used in the screening and probe is placed in a limited number of positions, for example in no more than 2–3 positions. Alternatively or additionally, in order to reduce noise due to irregularities in the measurement procedure, e.g., gel spreading, probe contact with the breast, etc., the probe is placed on a plurality of locations of the breast and in each location a dielectric parameter of the patient as a whole is determined. The dielectric parameter values of the different regions are then summed or averaged to reduce the noise. The weights used in averaging may be equal for all the measurements or may differ according to the quality of the measurements, for example as a function of a contact quality measure determined for the positioning of the probe. Alternatively to averaging the dielectric parameter values, the raw data collected in some or all of the positions may be averaged to reduce the noise. Optionally, the positions of the probe used for collecting the local impedance data are those which are known to have less noise affects. Such positions are optionally included in the upper surface of the breast and/or in the surface of the breast distanced from the other breast, where placing the probe is relatively simple and therefore involves less measurement noise.

In those embodiments in which local impedance measurements are accumulated from a plurality of positions, a value of the same dielectric parameter (or parameters) is optionally determined for all the probe positions. Alternatively, different parameters are determined for different positions.

In some embodiments of the invention, one or more regions of the breast, such as the nipple and/or areola areas, are identified as good predictors of breast cancer for the entire breast or even for both breasts of the patient. The impedance parameters of these regions are optionally different from the parameters used for other breast positions.

In some embodiments of the invention, the breast positions include areas from both breasts of the patient. A score generated based on the measurements optionally provides an indication on the probability of the patient having breast cancer without relating to which breast may have the cancer. One use of the present invention is in screening and referral to other modalities for further testing and localization of the lesion, if any. As such, the indication of the breast in which the lesion is present is less important for screening than the indication that additional tests are required.

It is noted that it is known in the art that finding LCIS (labula carcinoma in sito) in a breast can serve as a marker for possible or future cancers not only in the breast for which it was found. Without being bound by any explanation, it may be that the sensitivity of measurements as described herein made in one breast can act as a indicator for the other breast as well.

In some embodiments of the invention, the score is determined as an additive function of the values of the dielectric parameters. Optionally, the additive function comprises an averaging function, giving the same weight to each of the positions of the probe. Alternatively or additionally, the averaging function gives different weight to different positions of the probe, for example according to the proximity of the positions to the nipple and/or the contact quality at the position.

An aspect of some embodiments of the present invention relates to a method of providing a breast cancer risk score to a patient, based on dielectric measurements. The method includes determining values for at least first and second dielectric parameters, which are not directly related to a suspected lesion. In determining the score, the determined value of the first dielectric parameter is compared to a threshold, which is selected responsive to the measured value of the second dielectric parameter.

In some embodiments of the invention, the first and second dielectric parameters are not related to an impedance map or matrix of the breast. Alternatively or additionally, they are related to an image map, but are not related to any suspected or actual position of a lesion. Optionally, the first parameter comprises a characteristic frequency, for example a frequency at which the imaginary admittance has a maximum or one of a predetermined group of frequencies at which the imaginary admittance has a maximum.

In some embodiments of the invention, the first parameter is a function of the shape of a high admittance area in the vicinity of the nipple. This dependence may be additionally to or instead of the non-imaging methodology described above. In this case the first parameter would be based on an image, but would not be based on determination of a suspected cancer site.

In some embodiments of the invention, the second parameter comprises a phase of the impedance at one or more frequencies, optionally at the frequency of the second parameter.

In some embodiments of the invention, the patient is classified as belonging to one of a plurality of groups, each group having a separate threshold. Optionally, the threshold of each group is adjusted according to clinical data on other women belonging to the group. In some embodiments of the invention, the threshold of each group is adjusted so as to meet a desired specificity and/or sensitivity of the group. Optionally, the threshold of each group is a function of the size of the group and the distribution of cancer cases in the group (according to the value of the first parameter). The thresholds of the groups are optionally set together so that the overall specificity and/or sensitivity, for both groups together, reaches a desired level. Alternatively, the thresholds of all the groups are set to achieve a same sensitivity.

Various aspects of some embodiments of the invention are related to methods and apparatus for simplifying the procedures related to acquiring data for impedance based screening, imaging or diagnosis.

An aspect of some embodiments of the present invention relates to an apparatus for breast cancer examination, based on AC electrical signals, which determines an indication on the quality of the contact between a breast and a probe used to measure electrical signals from the breast. Although a probe for collecting electrical signals from the breast is easily placed by an operator as there is generally easy access of the probe to the breast, a determination of the quality of the contact is proposed herein to enhance the measurement results.

In some embodiments of the invention, the apparatus includes a display (or other output unit) that provides an indication on the quality of the contact of the probe with an examined breast. Optionally, the apparatus additionally includes a second output unit that provides an indication on the cancer risk of patients.

In some embodiments of the invention, the display provides a multi-level (i.e., including at least three different possible values) indication. Optionally, the multi-level display provides an indication on a single scale, e.g., ranging from very bad to very good. A physician operating the apparatus optionally adjusts the placement of the probe until a sufficient level of contact quality is achieved and optionally the contact has a stable quality level.

Alternatively or additionally, the multi-level display comprises an impedance image of the breast under the probe, which image is determined and/or displayed for analysis of the contact quality of the probe. In some embodiments of the invention, each pixel in the image is indicative (single or multi-level) of the contact quality of one of the elements of a multi-element probe used to acquire the impedance signals.

In some embodiments of the invention, the apparatus automatically controls collection and/or analysis of data for cancer risk determination of the patient, based on the determined contact quality indication. Optionally, the apparatus automatically determines when the impedance results are sufficiently stable to allow cancer score determination. Such stability is especially required when the measurements are used to provide a score, as opposed to when the measurements are used for image display, in which case the operator can easily determine the stability from the displayed image.

An aspect of some embodiments of the present invention relates to a method of acquiring impedance measurements from a patient, using a measurement probe. The method includes applying one or more first electrical signals having a first characteristic, for determining the quality of the contact between the probe and the patient, and applying one or more second signals, having a second characteristic different from the first, for determining at least one dielectric parameter used to determine a medical state of the patient, and not for determining the contact quality of the probe. Optionally, the signals having the first characteristic are not used for determining the medical state of the patient.

In some embodiments of the invention, the first and second characteristics comprise different frequencies. Optionally, the first electrical signals for determining the contact quality include signals at a plurality of frequencies. The second signals used for determining the at least one dielectric parameter optionally include fewer frequencies than the first electrical signals, optionally only two or one frequencies. Alternatively or additionally, the different frequencies of the first electrical signal are applied together in a broadband signal, while the frequencies of the second signals are applied separately in single band signals.

Alternatively or additionally, the first and second signals differ in their amplitude. For example, in determining the contact quality, signals of lower amplitude may be used, as the accuracy may be less important.

Another method of determining contact quality, in accordance with an embodiment of the invention utilizes the signal to noise ratio of electrical signals acquired as an indicator of contact quality. The method includes acquiring electrical signals from the patient and determining a signal to noise ratio (SNR) of the acquired signals. In some embodiments of the invention, a contact quality indication is determined and displayed, responsive to the SNR. The contact quality indication may depend solely on the SNR or may depend on one or more other quality dielectric parameters, such as stability or the range of the measured values. Optionally, the values of the one or more dielectric parameters are determined and/or considered valid only if the SNR has a sufficient value.

An aspect of some embodiments of the present invention relates to a method of determining a contact quality between a patient and a probe, used for collecting electrical signals from the patient. The method includes determining the pressure of the contact between the probe and the patient and determining the contact quality responsive to the determined pressure.

An aspect of some embodiments of the invention is related to a probe having a structure adapted for sensing signals from a nipple region. In an embodiment of the invention, electrodes having a hole or depression formed therein with a diameter suitable for insertion of the tip of the nipple are used. Some of these embodiments utilize multi-element probes and others utilize a single electrode probe having a diameter small enough to encompass only areola or a portion thereof. In an exemplary embodiment of the invention, a probe comprises two rings of different diameters. A first ring has a small diameter enough to encompass only the areola or a portion thereof. A second ring has a larger diameter, such that it does not encompass any part of the areola, so that the signals it senses represent non-nipple areas. The signals from the inner ring are used for testing with the signals from the outer ring used for normalization or other comparison.

In some embodiments of the invention, the probe includes an additional ring whose position and size is such that the inner and outer portions of the areola are measured separately. These measurements may be compared and/or combined in the risk determination.

In some embodiments of the invention, each ring includes a single contiguous electrode. Optionally, the width of the rings are adjusted such that both the rings have substantially the same surface area. Alternatively or additionally, portions of the larger ring are covered by an insulator so that the conducting contact area of the rings with the breast is substantially the same. Further alternatively or additionally, the rings have different contact areas with the breast and the collected signal values are adjusted accordingly.

Alternatively to including a single contiguous electrode, one or both of the rings may include a plurality of sensing elements mounted on the ring. Using a plurality of elements allows determination of the contact quality of each element separately, so that elements without proper contact may be compensated for and/or the contact may be corrected by an operator.

In some embodiments of the invention, the electrode is a circular, square, rectangular or other shaped electrode having an area small enough so that it is only covers a portion of the areola and not the surrounding tissue or the tip of the nipple.

An aspect of some embodiments of the present invention relates to determining a breast cancer risk score for a patient. Values of a dielectric parameter are determined for a plurality of frequencies, and the score is determined as a function of the values of the different frequencies. In some embodiments of the invention, the score is a function of the maximal or average value of the parameter. Performing the measurements over a plurality of frequencies provides robustness to the dielectric parameter, in case of a measurement problem for one or more of the frequencies.

An aspect of some embodiments of the present invention relates to a method of determining a portion of a breast from which signals are to be used for determining the state of the breast. The method includes placing a multi-element probe on the patient, and acquiring signals at one or more first frequencies. The signals of the one or more first frequencies are used in selecting a sub-group of the elements of the multi-element probe, such as the element touching the areola or those that have poor contact. A value of a dielectric parameter is determined based on measurements from the selected elements, at one or more second frequencies, and the dielectric parameter is used in determining the state of the breast. The second and first frequencies are generally not the same. Optionally, the first frequency is a lower frequency.

In some embodiments of the invention, the selected elements are included in a contiguous region, for example they represent the areola, which is well differentiated at low frequencies, which have high contrast between nipple and non-nipple areas. Alternatively, the selected elements are not necessarily adjacent each other, for example when the selection is based at least partially on the quality of the contact.

As used herein, when reference is made to a measurement based on the nipple or the areola, such measurements may include normalization and/or comparison to areas out of the nipple.

There is therefore provided in accordance with an embodiment of the invention, a method of breast examination of a patient, comprising providing electrical signals to a portion of the patient, sensing electrical signals from a nipple of a breast of the patient, determining a value of a characteristic dielectric parameter for the breast, responsive to electrical signals sensed from the nipple, determining a cancer risk score responsive to the value of the dielectric parameter, wherein the dielectric parameter based on nipple signals is treated differently from any dielectric parameters based on signals sensed from outside the nipple and providing an indication related to the cancer risk score to an operator.

Optionally, the dielectric parameter is determined only utilizing signals sensed at the nipple or areola. Optionally, the cancer risk is determined only utilizing signals sensed at the nipple and in an area within 1 cm from the edge of the areola. Optionally, the cancer risk is determined only utilizing signals sensed at the areola and in an area within 1 cm from the edge of the areola. Optionally, the dielectric parameter is determined utilizing signals sensed at the nipple and at other portions of the breast. Optionally, signals sensed at different portions of the breast outside the nipple and the areola are added or averaged in determining the dielectric parameter of the breast. Optionally, local dielectric parameters are computed for each portion outside the areola and wherein the characteristic dielectric parameter is responsive to the sum or average of the local characteristic values. Optionally, the cancer risk is determined only utilizing signals sensed by a single placement of a probe on the breast. Optionally, sensing the electrical signals comprises sensing through a surface multi-element probe.

There is further provided in accordance with an embodiment of the invention, a method of breast examination of a patient, comprising providing electrical signals to a portion of the patient, sensing electrical signals from an area of the breast, including at least a portion of the areola, differentiating between signals received from the areola and regions external to the outer edge of the areola, determining a value of a first characteristic dielectric parameter for the breast, responsive to only electrical signals from the nipple, determining a cancer risk score responsive to the value of the first dielectric parameter and providing an indication related to the cancer risk score to an operator.

Optionally, the method includes determining a value of a second characteristic dielectric parameter for the breast, responsive to electrical signals sensed at the external regions, the cancer risk score is responsive to the value of the first and second dielectric parameter. Optionally, differentiating comprises differentiating on the basis of at least some of the sensed signals. Optionally, differentiating comprises determining an outer periphery of the areola. Optionally, determining the outer periphery comprises finding an edge on a map of signal values or impedance related values. Optionally, differentiating comprises differentiating based on low frequency signals. Optionally, sensing the electrical signals is performed through a multi-element surface probe and wherein differentiating comprises selecting pixels having values of a dielectric parameter above an average value of the pixels by at least a predetermined margin.

There is further provided in accordance with an embodiment of the invention, a method of differentiating between portions of the breast, comprising acquiring electrical signals from a plurality of areas on the breast, determining impedance values of the plurality of areas; and differentiating between the nipple and areas outside the nipple based on the impedance values.

Optionally, differentiating comprises determining an outer periphery of the areola. Optionally, determining the outer periphery comprises finding an edge on a map of signal values or impedance related values. Optionally, differentiating comprises differentiating based on low frequency signals. Optionally, sensing the electrical signals is performed through a multi-element surface probe and wherein differentiating comprises selecting pixels having values of a dielectric parameter above an average value of the pixels by at least a predetermined margin.

There is further provided in accordance with an embodiment of the invention, apparatus for breast cancer screening, comprising a source electrode adapted to provide electrical signals to the patient, a multi-element surface probe for sensing electrical signals from a breast of the patient, a processor operative to determine which signals were sensed by the probe from an areola area of the breast of the patient and to calculate a cancer risk score responsive to the signals sensed from the areola area and an output unit operative to provide an indication related to the cancer risk score. Optionally, the processor also determines signals not sensed from an areola area and provides the score responsive to the signals sensed from the non-areola area.

There is further provided in accordance with an embodiment of the invention, apparatus for breast examination of a patient, comprising a source electrode adapted to provide electrical signals to the patient, a sensing unit including a surface probe capable of sensing electrical signals from a nipple area of a breast of the patient, a processor operative to determine a value of a nipple dielectric parameter, responsive to electrical signals sensed by the sensing unit from a nipple area of at least one breast of the patient, and to calculate a cancer risk score responsive to the value of the nipple dielectric parameter and an output unit operative to provide an indication related to the cancer risk score.

Optionally, the processor is adapted to determine which signals sensed by the sensing unit were acquired from the nipple. Optionally, the sensing unit is adapted for proper placement on the nipple. Optionally, the sensing unit includes an indent or hole for receiving the tip of the nipple, to improve contact of the sensing unit with the areola. Optionally, the sensing unit comprises an annular probe of a diameter such that it fits on the areola of patients. Optionally, the at least one electrode includes at least one ring electrode centered at the hole or indent. Optionally, the at least one ring comprises a ring having an outer diameter small enough so that it sits completely on the areola. Optionally, the at least one ring comprises a second ring having an inner diameter large enough so that it does not sit on the areola.

There is further provided in accordance with an embodiment of the invention, a sensing unit for measurement of the breast impedance, comprising a base, at least one electrode situated on the base and an indent or hole for receiving the tip of the nipple, to improve contact of the sensing unit with the areola.

Optionally, the at least one electrode includes at least one ring electrode having a centered at the hole or indent. Optionally, the at least one ring comprises a ring having an outer diameter small enough so that it sits completely on the areola. Optionally, the at least one ring comprises a second ring having an inner diameter large enough so that it does not sit on the areola.

There is further provided in accordance with an embodiment of the invention, a method of screening for breast cancer, comprising testing a plurality of asymptomatic women by measuring at least one electrical impedance characteristic on at least one breast, the asymptomatic woman being classified as belonging to a first group having a first risk factor for breast cancer and re-classifying some of the women as belonging to a second group having a second risk factor greater than the first risk factor, based on the at least one impedance characteristic, the second group has a risk factor of at least twice that of the first group, but less than 15 times that of the first group and fewer than 60% of those in the first group that have breast cancer are reclassified into the second group.

Optionally, the second group has a risk factor at least 5 times or even ten times as high as that of the first group. Optionally, the first group consists of a general population of women between 15 and 40 years old optionally between 20 and 35 years old. Optionally, more than 20% percent of women having cancer in the first group are re-classified in the second group. Optionally, more than 25% percent of women having cancer in the first group are re-classified in the second group. Optionally, more than 30% percent of women having cancer in the first group are re-classified in the second group. Optionally, fewer than 50% of women having cancer in the first group are re-classified in the second group. Optionally, fewer than 40% of women having cancer in the first group are re-classified in the second group. Optionally, up to 10% of the women in the first group not having cancer are placed in the second group. Optionally, between 5% and 10% of the woman in the first group, not having cancer are placed in the second group.

There is further provided in accordance with an embodiment of the invention, apparatus for breast cancer screening, comprising a probe for acquiring electrical signals from a breast of a patient, belonging to a low risk group for breast cancer, having a first risk factor for having breast cancer and a processor adapted to determine at least one dielectric parameter value responsive to signals acquired by the probe and to classify the patient as to whether she belongs to a high risk group, having a second risk factor of having breast cancer greater than the first risk factor, based on the at least one dielectric parameter, the processor is calibrated to classify less than 50% of women having cancer detectable by mammography in the low risk group as belonging to the high risk group and wherein the high risk group has a risk factor of at least twice that of the low risk group, but less than 15 times that of the low risk group.

Optionally, the processor is calibrated to classify less than 45%, 40% or even 35% of women having cancer detectable by mammography in the low risk group as belonging to the high risk group. Optionally, the processor is calibrated to classify less than 10% of the women in the low risk group as belonging to the high risk group.

There is further provided in accordance with an embodiment of the invention, a method of screening for breast cancer, comprising testing a plurality of asymptomatic women by measuring at least one electrical impedance characteristic on at least one breast, the asymptomatic woman being classified as belonging to a first group having a first risk factor for breast cancer and re-classifying some of the women as belonging to a second group having a second risk factor greater than the first risk factor, based on the at least one impedance characteristic, fewer than 10% of the women in the first group are reclassified into the second group. Optionally, fewer than 50% of the women in the first group that have cancer are reclassified into the second group.

There is further provided in accordance with an embodiment of the invention, a method of screening for breast cancer, comprising determining at least one electrical impedance related characteristic for a breast of a patient, the at least one impedance characteristic being determined by impedance measurements at at least one portion of the breast, without reference to an impedance related map of the breast, except, optionally, to determine an external feature of the breast to be used in defining the portion and classifying the patient as requiring additional testing, responsive to the value of the characteristic.

Optionally, the method includes determining at least one second electrical impedance related characteristic for a second breast of the patient, the impedance characteristic being determined by impedance measurements of a portion of the second breast, without reference to an impedance related map of the second breast, except, optionally, to determine an external feature of the breast to be used in defining the position and classifying the patient as requiring additional testing, responsive to the value of the first and second characteristic, wherein classifying is not based on a difference between the first and second characteristics.

There is further provided in accordance with an embodiment of the invention, a method of screening for breast cancer, including determining at least one first electrical impedance related characteristic for a first breast of a patient, determining at least one second electrical impedance related characteristic for a second breast of a patient, and classifying the patient as requiring additional testing, responsive to the value of the first and second characteristics, wherein classifying is not based on a difference between the first and second characteristics.

Optionally, classifying is performed for each breast separately and wherein the patient is classified as requiring further testing if either breast indicates such further testing. Optionally, the characteristics for the two breasts are averaged and the classification is based on the averaged value. Optionally, the at least one portion of the breast includes one or both of the nipple and areola of the respective breast. Optionally, the at least one portion is limited to the nipple and of the respective breast. Optionally, the at least one portion includes one or more additional portions of the breast not including the nipple. Optionally, the additional portions are limited to areas within 1 cm of the areola. Optionally, determining includes averaging the values of the characteristic measured at the additional portions. Optionally, the additional portion excludes the nipple tip. Optionally, the nipple portion is determined by using an electrode shaped to include only desired regions. Optionally, a determination of the area of the is made based on an impedance map. Alternatively or additionally, a determination of the area of the nipple is made based on an impedance map. Optionally, classifying the patient comprises providing a binary rating on whether the patient belongs to a high risk group. Optionally, classifying the patient comprises providing a multi-level rating.

Optionally, the patient is originally classified as being in a first risk group having a first risk factor and wherein classifying comprises re-classifying the patient as a member of a second risk group, for which a diagnosis is not made, but for which the risk justifies the additional testing, the second risk group having a second risk factor greater than the first risk factor. Optionally, the second group has a risk of greater than 2 but less than 15, the first risk factor.

There is further provided in accordance with an embodiment of the invention, apparatus for breast cancer screening, comprising an electrode for applying electrical signals to a patient, a probe for acquiring impedance signals from a breast of the patient, responsive to signals applied from the electrode, a processor adapted to determine at least one electrical impedance related characteristic for the breast of the patient, responsive to signals acquired by the probe, without reference to an impedance related map of the signals acquired by the probe, except, optionally, to classify signals acquired by the probe as to an external feature of the location from which the signals were collected, and to determine a score as to whether the patient belongs to a high risk group responsive to the determined at least one characteristic; and an output unit adapted to provide an indication as to whether the patient belongs to a high risk group.

There is further provided in accordance with an embodiment of the invention, apparatus for breast cancer screening, including a probe for acquiring electrical signals from the breasts of a patient and a processor adapted to determine for each breast of the patient a respective dielectric parameter value of the breast, responsive to signals acquired by the probe and to classify the patient as to whether additional testing is required, responsive to the values of the determined parameter values, wherein the classifying is not based on a difference between the parameter values.

Optionally, the processor determines values of the same dielectric parameter for both breasts. Optionally, the processor is adapted to classify the patient as to whether additional testing is required, without relation to an impedance map of the breasts. Optionally, the processor is adapted to classify the patient based on an additive function of the parameter values of the breast. Optionally, the processor is adapted to classify each breast separately and the patient is classified as requiring further testing if either breast is classified as requiring further testing. Optionally, the processor is adapted to classify each breast separately and the patient is classified as requiring further testing based on an average of the classifications of the two breasts.

There is further provided in accordance with an embodiment of the invention, a method of providing a breast cancer risk score for an asymptomatic patient, comprising applying electrical signals to the asymptomatic patient, acquiring electrical signals from the breast, responsive to the applied signals, determining a value of a first dielectric parameter based on the acquired signals, determining a value of a second dielectric parameter, responsive to the acquired signals, selecting a threshold to which the second dielectric parameter is to be compared, responsive to the value of the first parameter; and determining a breast cancer risk score, by comparing the dielectric parameter to the selected threshold.

Optionally, determining the first dielectric parameter comprises determining a frequency characteristic of the dielectric parameter. Optionally, determining the first dielectric parameter comprises determining a peak frequency of an imaginary portion of an admittance determined from the acquired signals. Optionally, determining the second frequency comprises determining at the phase of the admittance at the determined peak frequency. Optionally, determining the first dielectric parameter comprises determining a parameter without relating to an impedance map of the breast, other than to determine an external feature of a portion of the breast at which the signals are acquired. Optionally, acquiring the signals comprises acquiring through a surface multi-element probe and wherein determining the first dielectric parameter comprises determining a parameter without comparing values determined from different elements of the probe, other than to determine an external feature of a portion of the breast at which the signals are acquired. Optionally, determining the second dielectric parameter comprises determining a phase parameter.

Optionally, selecting the threshold comprises determining a group to which the patient belongs based on the first parameter and selecting the threshold responsive to the determined group. Optionally, the threshold responsive to the determined group is generated based on clinical data of the determined group. Optionally, the threshold is selected so that the score has a high specificity.

There is further provided in accordance with an embodiment of the invention, apparatus for breast cancer screening, including a probe for acquiring electrical signals from a breast of a patient and a processor adapted to determine first and second dielectric parameter values responsive to signals acquired through the probe, without relation to an impedance map of the breast, to select a threshold based on the first parameter value and to provide a breast cancer risk score responsive to a comparison of the value of the second parameter value to the threshold.

There is further provided in accordance with an embodiment of the invention, apparatus for providing a clinical indication on a breast of a patient, comprising a source of electrical signals adapted to apply AC electrical signals to the patient, a probe adapted to acquire AC electrical signals from the patient, responsive to the applied signals, a processor adapted to determine a contact quality level of the contact between the probe and the patient, responsive to signals acquired by the probe, a first output element adapted to provide an indication of the determined contact quality level.

Optionally, the first output element is connected to a signal acquiring unit, such that the processor automatically acquires information suitable for providing a clinical indication of the health of the patient when the determined contact is above a predetermined contact quality level. Optionally, the first output element comprises a human interface. Optionally, the first output unit is adapted to provide an indication on a multi-scale level of at least three possible values.

Optionally, the probe comprises a multi-element probe and wherein the first output unit is adapted to provide an image of contact quality indication, including a pixel corresponding to the contact quality of substantially each element of the probe. Optionally, the contact quality level is responsive to a predetermined plurality of consecutive similar measurements which are made and which show a stable acquired signal level. Optionally, the probe is a multi-electrode probe and wherein the contact quality level for the probe is responsive to the number of the electrodes that make quality contact. Optionally, the contact quality level is responsive to a measured pressure of the probe against the breast. Optionally, the contact quality level is responsive to a signal to noise level of the signals. Optionally, the apparatus includes a second output element adapted to provide an indication on the medical state of the breast.

There is further provided in accordance with an embodiment of the invention, a method of acquiring electrical signals from a patient, comprising placing a probe on a surface of the patient, applying first source electrical signals having a first characteristic to the patient, acquiring first acquired electrical signals by the probe responsive to the applied first source electrical signals, applying second electrical signals having a second characteristic, different from the first characteristic, to the patient, acquiring second acquired electrical signals by the probe responsive to the applied second source electrical signals, determining a contact quality of the probe responsive to the first acquired signals, but not responsive to the second acquired electrical signals and providing an indication on a medical state of the patient, responsive to the second acquired electrical signals.

Optionally, the indication on the medical state of the patient is determined without relation to the acquired first acquired electrical signals. Optionally, applying the applied electrical signals of the first characteristic comprises applying an electrical signal including a plurality of frequencies concurrently. Optionally, applying the applied electrical signals of the second characteristic comprises applying signals including one or more frequencies, each frequency signal being applied separately. Optionally, the signals having the first and second characteristics differ in amplitude. Optionally, the signals having the first characteristic include at least one frequency not included in the signals of the second characteristic. Optionally, the signals having the second characteristic include at least one frequency not included in the signals of the first characteristic. Optionally, the contact quality level is responsive to a predetermined plurality of consecutive similar measurements which are made and which show a stable acquired signal level. Optionally, the probe is a multi-electrode probe and wherein the contact quality level for the probe is responsive to the number of the electrodes that make quality contact.

Optionally, the contact quality level is responsive to a measured pressure of the probe against the breast. Optionally, the contact quality level is responsive to a signal to noise level of the acquired signals. Optionally, the contact quality level is responsive to the acquired signals having values within a predetermined range.

There is further provided in accordance with an embodiment of the invention, a method of determining a quality of contact of a probe to a patient, comprising placing a probe on a surface of the patient, applying electrical signals to the patient acquiring electrical signals by the probe responsive to the applied electrical signals, determining a signal to noise ratio of the acquired signals and determining a contact quality of the probe responsive to the signal to noise ratio. Optionally, the probe comprises a multi-element probe and wherein the signal to noise ratio is determined as the minimal ratio determined for a plurality of the elements.

There is further provided in accordance with an embodiment of the invention, a method of determining a quality of contact of a probe to a patient, comprising placing a probe adapted to acquire electrical signals for medical diagnosis on a surface of the patient, determining a parameter of the pressure of the probe on the surface of the patient and determining a contact quality of the probe responsive to the determined pressure parameter.

Optionally, the method includes acquiring electrical signals from the patient through the probe, responsive to the contact quality having a sufficient level. Optionally, acquiring the electrical signals comprises acquiring automatically responsive to the contact quality having a sufficient level.

There is further provided in accordance with an embodiment of the invention, apparatus for acquiring electrical signals from a patient, comprising a probe including a plurality of sensing elements adapted to sense electrical signals, at least one pressure sensor adapted to determine the pressure of the probe on a patient surface and an output element adapted to provide an indication of the contact quality level of the probe responsive to readings of the at least one pressure sensor.

Optionally, the at least one pressure sensor is mounted on the probe. Optionally, at least one of the sensing elements is mounted on a base of the probe through a pressure sensor.

There is further provided in accordance with an embodiment of the invention, a method of determining a contact quality of a probe to a patient, comprising placing a probe on a surface of the patient, applying electrical AC signals to the patient, repeatedly acquiring AC signals through the probe, responsive to the applied signals and determining a contact quality of the probe on the surface, responsive to the stability of the values of the repeatedly acquired AC signals. Optionally, determining the contact quality comprises determining that the contact quality is sufficient responsive to receiving similar values in at least 10 repeated acquired signals.

There is further provided in accordance with an embodiment of the invention, apparatus for acquiring electrical signals from a patient, comprising a probe suitable for placement on a surface of the patient, a source electrode that is suitable for applying electrical applied signals to a patient, the applied signals being suitable for impedance measurements, a controller that in a first mode is operative to apply first applied electrical signals having a first characteristic to the patient, acquire first acquired electrical signals by the probe responsive to the first applied electrical signals; and determine a contact quality of the probe responsive to the first acquired signals; and in a second mode is operative to apply second applied electrical signals having a second characteristic, different from the first characteristic, to the patient, acquire second acquired electrical signals by the probe responsive to the applied second electrical signals and provide an indication on a medical state of the patient, responsive to the acquired second electrical signals, the determination of contact quality is not responsive to the second electrical signals.

Optionally, the controller determines the indication on the medical state of the patient without relation to the first acquired electrical signals. Optionally, the electrical signals of the first characteristic comprise an electrical signal including a plurality of frequencies applied concurrently. Optionally, electrical signals of the second characteristic comprise signals including one or more frequencies, each frequency signal being applied separately. Optionally, the signals of the first and second characteristics differ in amplitude. Optionally, the signals of the first characteristic include at least one frequency not included in the signals of the second characteristic. Optionally, the signals of the second characteristic include at least one frequency not included in the signals of the first characteristic. Optionally, the controller determines the contact quality level responsive to a predetermined plurality of consecutive similar measurements which are made and which show a stable acquired signal level. Optionally, the probe is a multi-electrode probe and wherein the controller determines the contact quality level for the probe responsive to the number of the electrodes that make quality contact.

Optionally, the apparatus includes a pressure sensor and wherein the controller determines the contact quality level responsive to a measured pressure of the probe against the breast. Optionally, the controller determines the contact quality level responsive to a signal to noise level of the signals. Optionally, the controller determines the contact quality level responsive to the signals having values within a predetermined range. Optionally, the controller acquires the electrical signals automatically responsive to the contact quality having a sufficient level.

There is further provided in accordance with an embodiment of the invention, apparatus for determining quality of contact of a probe with a patient, comprising a probe suitable for placement on a surface of the patient, a source electrode that is suitable for applying electrical applied signals to a patient, the applied signals being suitable for impedance measurements, a controller that is operative to apply electrical signals to the patient via the source electrode, acquire electrical signals via the probe responsive to the applied electrical signals and determine a contact quality of the probe responsive to a signal to noise level of the acquired signals.

Optionally, the probe comprises a multi-element probe and wherein the signal to noise ratio is determined as the minimal ratio determined for a plurality of the elements. Optionally, the controller acquires electrical signals for determining a medical state of the patient automatically responsive to the signal to noise level having a sufficient level.

There is further provided in accordance with an embodiment of the invention, a method of breast examination of an asymptomatic patient, comprising providing electrical signals to a patient, sensing electrical signals from a plurality of non-adjacent breast areas of the patient, responsive to the provided electrical signals, combining the sensed electrical signals without comparing the signals sensed in different areas, determining a value of a characteristic dielectric parameter for the breast, responsive to the combined sensed electrical signals, determining a cancer risk score responsive to the value of the characteristic dielectric parameter and providing an indication related to the cancer risk score.

There is further provided in accordance with an embodiment of the invention, a method of breast examination of a patient, comprising providing electrical signals to a patient, sensing electrical signals from a plurality of breast areas of the patient, responsive to the provided electrical signals, determining a value of a characteristic dielectric parameter for each of the breast areas, responsive to the sensed electrical signals of the respective area, combining the values of the characteristic dielectric parameters without comparing the values of different areas, determining a cancer risk score responsive to the combined value of the characteristic dielectric parameter; and providing an indication related to the cancer risk score.

There is further provided in accordance with an embodiment of the invention, a method of breast examination of a patient, comprising providing electrical signals to a patient, sensing electrical signals from a plurality of breast areas of the patient, responsive to the provided electrical signals, determining a value of a characteristic dielectric parameter for each of the breast areas, responsive to the sensed electrical signals of the respective area, determining a cancer risk score for at least some of the areas responsive to the value of the characteristic dielectric parameter of the area, combining the scores of the different areas; and providing an indication related to the combined score.

Optionally, combining comprises combining using an additive function. Optionally, combining comprises averaging or summing. Optionally, combining comprises combining using a weighted average. Optionally, the characteristic dielectric parameter comprises a characteristic frequency. Optionally, the characteristic dielectric parameter comprises an impedance or admittance value. Optionally, the characteristic dielectric parameter comprises an impedance phase. Optionally, providing the score comprises providing a binary indication of whether the patient should be referred for further diagnostic testing. Optionally, providing the score comprises providing a score on a multi-level scale. Optionally, the plurality of areas comprise different pixels corresponding to sensing elements of a multi-element surface probe through which the signals are sensed. Optionally, the plurality of areas comprise areas corresponding to different substantially non-overlapping placements of a multi-element surface probe through which the signals are sensed. Optionally, the areas comprise multi-pixel areas.

Optionally, the areas comprise areas which differ in at least one external parameter not related to whether the breast is cancerous. Optionally, the plurality of areas comprise areas on a single breast. Optionally, the plurality of areas comprise at least two areas on different breasts of the patient. Optionally, the plurality of areas comprise at least one areola area and at least one non-areola area. Optionally, the patient is an asymptomatic patient.

There is farther provided in accordance with an embodiment of the invention, apparatus for breast examination of a patient, comprising a source electrode adapted to apply electrical signals to the patient, a probe for sensing electrical signals from a plurality of non-adjacent breast areas of the patient, responsive to signals applied by the source electrode, a processor adapted to combine the sensed signals from the plurality of areas, without comparing the signals sensed from different areas and to calculate a cancer risk score responsive to the combined signals; and an output unit operative to provide an indication related to the cancer risk score.

There is further provided in accordance with an embodiment of the invention, apparatus for breast examination of a patient, comprising a source electrode adapted to apply electrical signals to the patient, a probe for sensing electrical signals from a plurality of breast areas of the patient, responsive to signals applied by the source electrode, a processor adapted to determine a value of a characteristic dielectric parameter for each of the breast areas, responsive to the sensed electrical signals of the respective area, to combine the values of the characteristic dielectric parameters without comparing the values of different areas, and to calculate a cancer risk score responsive to the combined values; and an output unit operative to provide an indication related to the cancer risk score.

Optionally, the characteristic dielectric parameter comprises a characteristic frequency.

There is further provided in accordance with an embodiment of the invention, apparatus for breast examination of a patient, comprising a source electrode adapted to apply electrical signals to the patient, a probe for sensing electrical signals from a plurality of breast areas of the patient, responsive to signals applied by the source electrode, a processor adapted to determine a cancer risk score, indicating a probability of the patient having breast cancer, for each of the breast areas, responsive to the sensed electrical signals of the respective area, and to calculate a combined cancer risk score responsive to the cancer risk scores of the areas and an output unit operative to provide an indication related to the cancer risk score.

There is further provided in accordance with an embodiment of the invention, a method of determining a value of a dielectric parameter, characteristic of a medical state of a patient, comprising placing a multi-element probe on the breast of the patient, acquiring electrical signals at one or more first frequencies, from the patient through the probe, selecting a sub-group of elements of the probe responsive to the acquiring electrical signals at the one or more first frequencies; and determining a value of a dielectric parameter, based on signals acquired by the selected sub-group of elements, at one or more second frequencies, the first and second frequencies are not all the same.

There is further provided in accordance with an embodiment of the invention, a method of determining a dielectric parameter of a patient, comprising applying electrical signals of a plurality of frequencies to the patient, acquiring electrical signals from the patient responsive to the applied electrical signals, determining a value of a dielectric parameter, for each of the plurality of frequencies, responsive to the acquired electrical signals, calculating an average of the values of the dielectric parameter over the plurality of frequencies and providing a cancer risk score to the patient responsive to the calculated average.

Optionally, determining the value of the dielectric parameter comprises determining a value of a parameter not requiring analyzing an image.

BRIEF DESCRIPTION OF THE DRAWINGS

Exemplary non-limiting embodiments of the invention will be described with reference to the following description of the embodiments, in conjunction with the figures. Identical structures, elements or parts which appear in more than one figure are preferably labeled with a same or similar number in all the figures in which they appear, and in which.

DETAILED DESCRIPTION OF EXEMPLARY EMBODIMENTS

Figure 1:
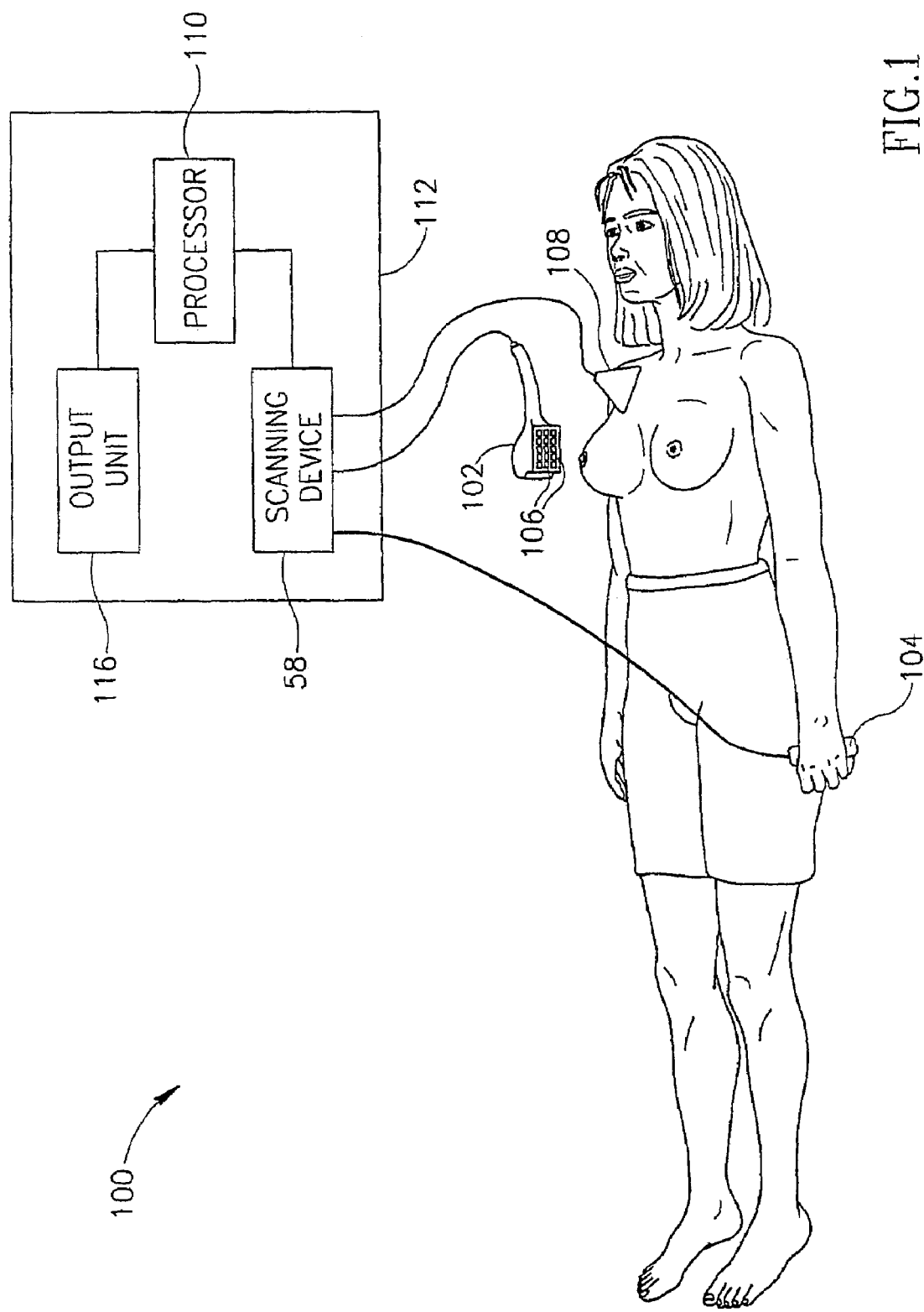
FIG. 1 is a schematic illustration of a breast examination system, in accordance with an exemplary embodiment of the present invention.

FIG. 1 is a schematic illustration of a breast examination system 100, in accordance with an exemplary embodiment of the present invention. Breast examination system 100 comprises a source electrode 104 adapted to apply electrical signals to a patient and a surface probe 102 adapted to sense electrical signals, induced by the applied signals, from a breast of a patient. Electrode 104 may comprise, for example, a hand held cylinder which is held by the patient and provides electrical signals to the patient through the hand.

Surface probe 102 optionally comprises a multi-element probe which includes a plurality of sensing elements 106. For clarity of FIG. 1, only a limited number of sensing elements 106 are shown. Although in some embodiments of the invention, only such a limited number of elements is used, in other embodiments of the invention more elements are used. The term surface probe refers herein to a probe, which fits on a single continuous surface of the breast. The element of a multi-element surface probe fit on a continuous surface of the breast, such that the elements are optionally distanced from each other by no more than about 2–4 times the size of the elements, usually by less than the size of the elements. Surface probe 102 is optionally of a size that covers a small portion of an average breast, for example 5–20%, since as described below, probe 102 optionally collects signals from one or more representative regions of the breast, rather than imaging the entire breast. Imaging the entire breast generally requires a relatively long procedure. Sensing elements 106 optionally have a small area, smaller than required for the accuracy of the procedure described below. The small area elements are optionally used in order to allow examination of their contact to the breast, before their values are used in the calculation procedure. For example, local contact problems may be due to small air bubbles. Alternatively or additionally, measurements from the small elements may be used to delineate the areola. In an exemplary embodiment of the invention, sensing elements 106 have an area of about 4×4 millimeters and are distanced from each other by about 0.4 mm.

In an exemplary embodiment of the present invention, surface probe 102 comprises a square, e.g., 8×8 or 16×16, array of sensing elements 106. Alternatively, surface probe 102 comprises a rectangular array of sensing elements. Further alternatively, the elements of surface probe 102 are organized in other shapes, for example in a circular shape.

In some embodiments of the invention, an additional electrode 108 is placed on the trunk of the patient's body closer to the breast than the source electrode 104. The additional electrode is optionally used to measure the voltage at a point close to the breast and thus cancel the effect of the path from source electrode 102 to the breast, and the contact impedance of source electrode 104, from the calculations. Alternatively or additionally, any other normalization methods are used, for example those described in U.S. patent application Ser. No. 10/033,017, entitled Diagnosis probe, filed 22 Oct. 2001, the disclosure of which is incorporated by reference.

In some embodiments of the invention, system 100 further comprises an electrical impedance scanning device 58 which controls the sensing of the impedance signals by sensing elements 106 and/or the applying of electrification signals to the patient from electrode 104. Scanning device 58 may be substantially any suitable electrical impedance scanning device known in the art, for example, a T-Scan™ 2000 Impedance Scanner marketed by TransScan, Israel, or any of the scanners described in U.S. Pat. Nos. 5,810,742, 4,458, 694, PCT applications PCT/IL00/00127, PCT/IL00/00839 and/or U.S. patent application Ser. No. 09/460,699, the disclosures of which documents are incorporated herein by reference.

A processor 110 optionally receives the signals sensed by sensing elements 106 and determines therefrom, a malignancy score of the examined breast, as described below. An output unit 116 optionally provides an indication of the malignancy score to the operator. In some embodiments of the invention, output unit 116 provides a binary score having only two possible values (e.g., "OK" or "high risk"). Optionally, output unit 116 includes an indicator which lights up, for example, an indicator light, stating that the tested patient is in a high risk group. Alternatively or additionally, output unit 116 includes different color indicators, which indicate different test results. For example a green light may indicate that the patient is not classified as belonging to a high risk group and a red light indicates that the patient belongs to a high risk group. In some embodiments of the invention, output unit 116 includes a LED display that states, for example, "additional tests" or "OK", as appropriate. Alternatively or additionally, output unit 116 includes other output interfaces, such as a speaker that provides sound indications. Alternatively or additionally, the malignancy score is selected from a multi-value scale.

In an exemplary embodiment of the invention, the malignancy score does not indicate the location of a possible anomaly. In some embodiments of the invention, system 100 does not attempt to determine the location of an anomaly but only to provide a general indication as to whether such an anomaly exists. Alternatively or additionally, system 100 does not relate directly to whether an anomaly exists but rather identifies a high risk population group, which requires periodic tests for breast cancer.

In addition to a score output, output unit 116 optionally provides one or more indications of the quality of the contact between surface probe 102 and the examined breast, as discussed in detail below.

In some embodiments of the invention, processor 110 is included in a single housing 112 with surface probe 102, output unit 116 and impedance scanning device 58. Optionally, housing 112 includes a socket adapted to connect to electrode 104. In some embodiments of the invention, housing 112 includes a compartment not shown) adapted to receive electrode 104 when not in use. Alternatively to including surface probe 102 in housing 112, housing 112 includes a socket adapted to connect to surface probe 102. Thus, the replacement of surface probe 102 is simplified, for example, if one-time surface probes 102 are used. Further alternatively, housing 112 includes a permanently connected cable for attachment to surface probe 102 or permanently connected to surface probe 102. Alternatively, scanning device 58 is included with probe 102, separate from processor 110.

Optionally, system 100 is light weight and/or portable, allowing simple movement of the system between locations. In some embodiments of the invention, housing 112 requires a relatively small space volume, such that it may be used, for example, in every physician's office, without requiring a large amount of storage space. System 100 is optionally of relatively low cost to further facilitate its wide distribution.

It is noted that the measurements performed using system 100 do not use ionizing radiation and are not significantly painful. Therefore, these tests are not expected to be objected to by patients. By having system 100 widely distributed, for example, in every women physician's clinic, the tests of system 100 may be applied to a relatively large percentage of the population, which visits physicians for periodic checkups and/or for other reasons.

Figure 2:
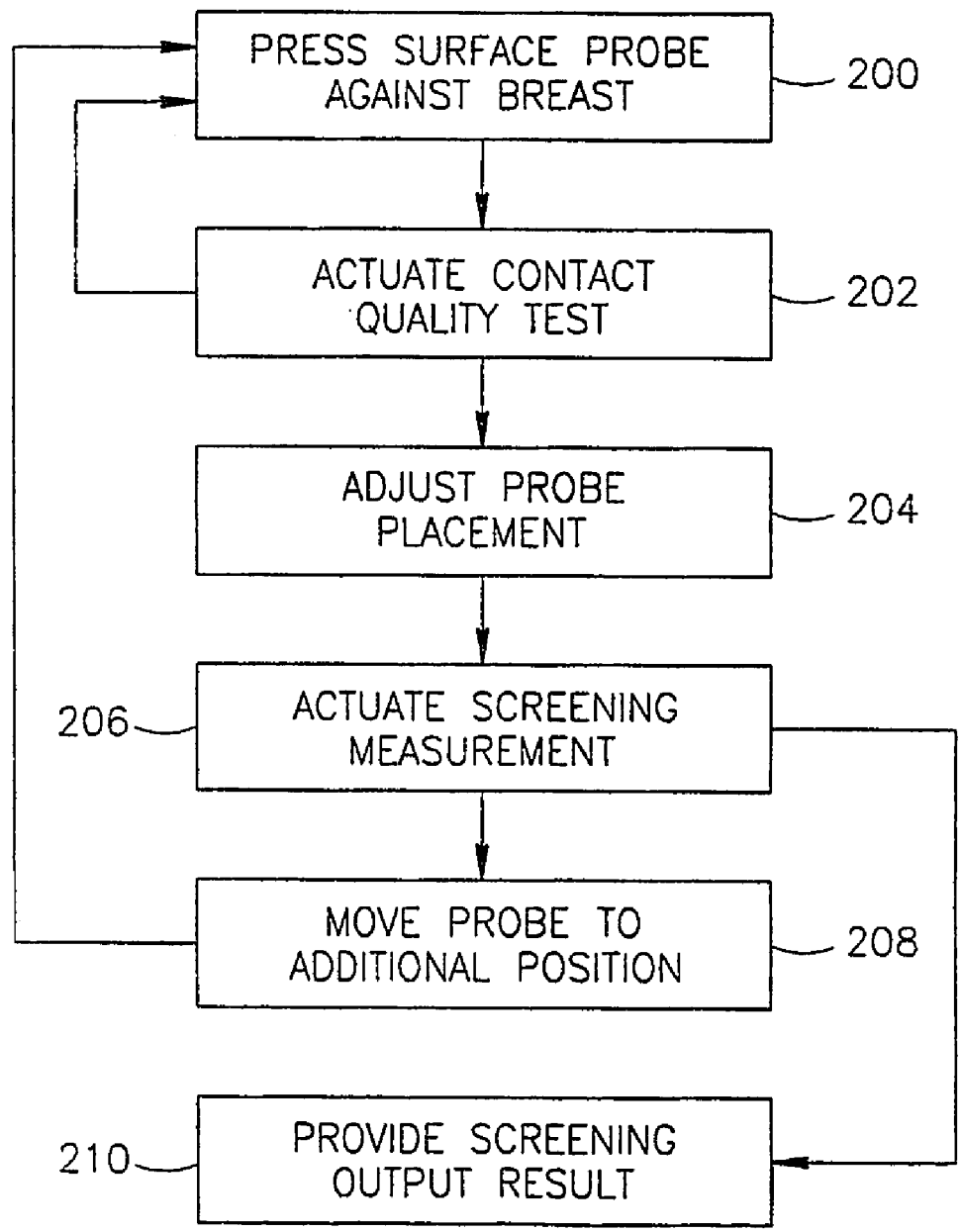
FIG. 2 is a flowchart of acts performed by a scanning operator during a cancer screening procedure, in accordance with an exemplary embodiment of the present invention.

FIG. 2 is a flowchart of acts performed by a scanning operator during a cancer screening procedure, in accordance with an exemplary embodiment of the present invention. Surface probe 102 is optionally pressed (200) against a central surface of breast 120, including the nipple. In some embodiments of the invention, the operator actuates (202) a testing of the contact quality of the probe. As discussed below, the contact quality testing optionally includes measuring electrical signals through the elements of probe 102 and checking that the measured values adhere to one or more predetermined requirements. The results of the contact quality testing are optionally displayed by output unit 116.

The operator optionally adjusts (204) the placement of probe 102, if necessary, until the contact quality is sufficient and stable. When a sufficient and stable contact quality is achieved, the operator actuates (206) a screening impedance measurement from the current position of probe 102. Alternatively, the screening impedance measurement is actuated automatically by system 100, when the contact quality is suitable. In some embodiments of the invention, probe 102 is moved (208) to one or more additional positions on the breast, and the actuating of the contact quality testing (202), the adjusting of the position (204) and the actuation of the screening impedance measurement (206) are repeated for each position of probe 102. Based on the measurements from the positioning on the nipple and the one or more other positions, an indication on whether the patient belongs to a high risk group for breast cancer, is optionally provided (210) through output unit 116.

In some embodiments of the invention, the method of FIG. 2 is used in conjunction with palpation. Optionally, a physician first performs palpation and if the palpation does not indicate a need of further tests, impedance tests in accordance with the method of FIG. 2 are carried out. Alternatively or additionally, impedance testing is performed before the palpation, so that the unrest of the breast in the first few minutes after palpation does not affect the impedance testing. In some embodiments of the invention, the impedance tests are performed twice or more and the highest cancer risk score from all the tests is used. Alternatively, the lowest score or the average score is used.

The method of FIG. 2 is optionally applied to asymptomatic women, who have a low probability of having cancer. The group of asymptomatic women is so large that it is generally not feasible to apply more expensive modalities (X-ray mammography, ultrasound) to all the women in the group. Using the method of FIG. 2, a high risk group can be identified which has a probability of having cancer higher by a factor of between about 2–20 than asymptomatic women. Alternatively or additionally, the method of FIG. 2 is applied to other groups of women who have low probabilities of having cancer, even if greater than the probability of asymptomatic women. Such groups may include women of specific ages, races, genetic data, disease family history, etc. The groups to which the impedance screening methods are applied are optionally groups which are too large to undergo X-ray mammography or which otherwise do not generally undergo mammography testing. The fact that a significant percentage of women who have cancer are missed, is offset by the numbers of women who would never undergo testing who are referred to such testing based on the present methodology.

While an impedance test is used in the exemplary embodiments of the invention, the idea of using a low sensitivity, relatively high selectivity test on low risk asympotic women can be applied in other modalities in which thresholds can be set to provide a significant sensitivity (>30, 35, 40 or 50%) and a relatively high selectivity (>90–95%). While such tests would not be definitive, they would increase the risk factor so that further testing would be indicated.

In some embodiments of the invention, the method of FIG. 2 is applied to young women as tests show that it is more effective on young women. In preliminary test results it has been found that the sensitivity for women below age 40 is about 60%, for women between 40–45 is about 29% and for women above 45 is only about 8%. On the other hand, the number of very young women (e.g., below 20 years) with breast cancer is very small such that it mat not be effective to scan all the women below age 20, even with system 100 which allows simple use. Therefore, in some embodiments of the invention, the method of FIG. 2 is recommended for women between the ages 20–45 or ages 25–40. It is noted, however, that the method of the present invention may be used on groups of older women who do not go for screenings of other modalities, provided that they will go for such screening if so recommended by system 100. If used for older women, the thresholds discussed below may be set to a lowest specificity that will still cause women to go for further tests if they are identified as belonging to a high risk group, so as to increase the sensitivity of the system.

Figure 3:
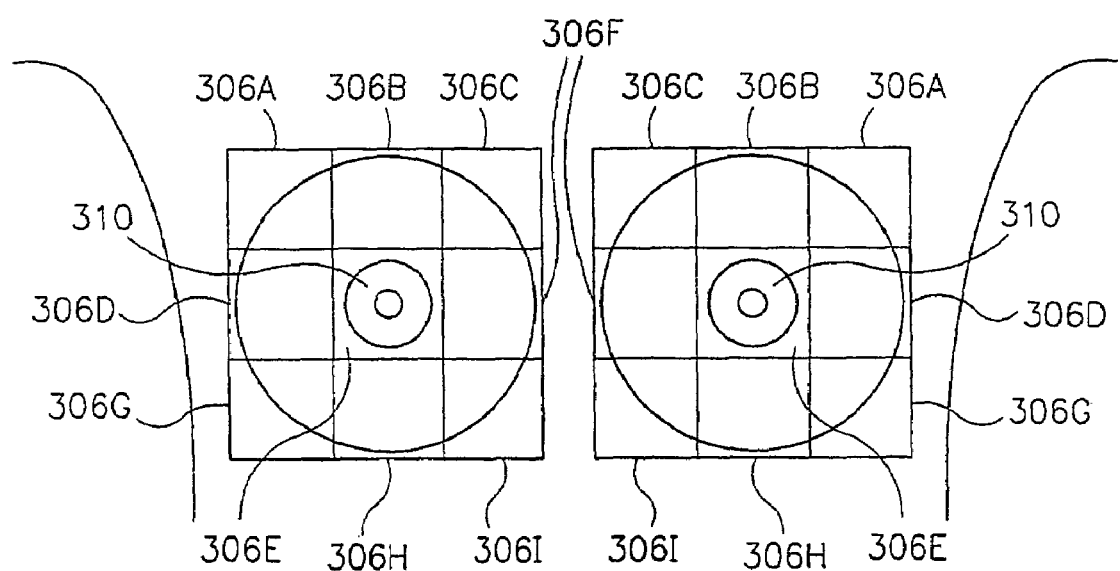
FIG. 3 is a schematic illustration of a patient's breasts and the positions thereon for placing an impedance probe, in accordance with an exemplary embodiment of the invention.

FIG. 3 is a schematic illustration of a patient's breasts and the positions thereon for placing an impedance probe, in accordance with an exemplary embodiment of the invention. Optionally, the right breast 302 and the left breast 304 are each virtually divided into nine sectors (marked 306A, 306B, . . . , 306I) of substantially the same surface area as probe 102. Optionally, measurements are acquired from a central sector 306E covering nipple 310. In some embodiments of the invention, measurements are gathered from one or more of the other sectors, for example from 3–4 out of 8 sectors. Optionally, the operator may select the additional sectors according to their convenience and/or according to where high contact testing scores are achieved. Alternatively, a predetermined set of sectors, for example, the three top sectors 306A, 306B and 306C and the external center sector 306D, are used for all patients, in order to achieve comparison between patients in similar conditions. The use of the top and central external sectors is generally easier, as these sectors allow easier access for probe 102.

In those embodiments in which measurements are acquired from a plurality of placements of probe 102 on different locations of the breast, the operator is optionally instructed to use a predetermined order of measurements so that the compared test results are acquired in as similar as possible conditions. Alternatively, the operator may actuate the measurements in any order. Optionally, an input interface receives from the operator an indication of the location on which probe 102 is placed. Alternatively, processor 110 automatically determines whether probe 102 was placed on central sector 306E, which includes the nipple, based on the impedance differences between the nipple and other breast areas.

It is noted that in accordance with some embodiments of the present invention it is not necessary to measure signals from the entire breast, as signals indicating that the examined patient belongs to a high risk group would appear throughout the entire breast and/or in a specific locality, such as around the nipple, and not necessarily in an area in which a malignant tumor develops.

In some embodiments of the invention, the procedure of FIG. 2 is performed for both breasts, and a separate score is given for each breast. Alternatively, a single score is provided for both breasts, the score being additive of the effects of both breasts or being a maximum or other function of the effects of both breasts. This alternative is based on the fact that the impedance effects which are indicative of having a high risk of breast cancer appear in some cases in both breasts in parallel, regardless of the breast in which a malignant tumor may develop. Further alternatively or additionally, the procedure of FIG. 2 is performed on only one of the breasts. Optionally, the patient or operator may select which breast is to be tested. Alternatively, the tests are always applied to a specific one of the breasts, e.g., the right breast.

Referring in more detail to pressing (200) probe 102 against the breast, optionally, a disposable gel interface, for example as described in PCT patent publication WO 01/64102, entitled Uniform, Disposable, Interface for Multi-Element Probe (the disclosure of which is incorporated by reference) is placed between probe 102 and the breast, so as to provide good electrical contact between probe 102 and the breast, while preventing direct contact between the probe and the breast, allowing safe use of probe 102 with a plurality of patients. Alternatively or additionally, probe 102 comprises a disposable breast interface, as described for example in U.S. Pat. No. 5,810,742 to Pearlman. Further alternatively or additionally, probe 102 in its entirety comprises a disposable probe, which is replaced for each patient. In some embodiments of the invention, probe 102 is cleaned and/or sterilized between test procedures. It is noted that the procedure of FIG. 2 is relatively simple, such that the procedure may be carried out by substantially any user, nearly without any training. The procedure of FIG. 2 may be carried out by a gynecologist, by any other physician, by a nurse, a technician or optionally even by the patient.

The measuring of the admittance from the nipple, provides a better indication of the malignancy of the breast, at least partially due to the lower impedance of the skin surrounding the nipple relative to other outer surfaces of the breast. By having a lower impedance, the nipple attracts currents from throughout the breast, thus providing from a single point an indication on the entire breast. Additionally, the high surface impedance of the skin, which generally masks the tissue impedance for low frequencies, is at least partially avoided. Furthermore, the nipple is at one end of the ducts. Since most cancers start at the ducts or the lobula, nipple conductivity is a good example of breast condition. In some embodiments of the invention, surface probe 102 includes a marking defining a point that is to be placed on the nipple.

Alternatively to using the same probe for measuring signals from the nipple and from other breast areas, a different probe is used for measuring impedance signals from the nipple. For example, a small probe may be used for the nipple while a larger probe is used for other breast areas. Alternatively, a circular probe with a narrow guard ring is used to limit the measurements from the probe of the nipple to the nipple area. Alternatively or additionally, a fixed annular area, i.e., having a ring electrode, is used as a standardized probe which covers only an annular portion of the nipple, i.e., a portion of the areola. In some embodiments of the invention, a probe having a depression at the tip of the nipple is used. This reduces or avoids the pressing of the nipple into the breast. While the tip is thus not generally imaged, the amount of the areola that is imaged is greatly increased. The probe may include an imaging capability to aid in placement. Alternatively, the probe is a single electrode probe and the score is determined based on the impedance measured by the single electrode. In some embodiments of the invention, a voltage is applied to the guard ring to at least partly cancel cupping effects.

Referring now to the contact quality testing as performed by system 100, in some embodiments of the invention, in response to actuation (202) of the testing, a signal of a plurality of frequencies is applied to electrode 104. Optionally, the applied frequencies are included in a wide band, for example ranging from 100 Hz to above 100 kHz. Alternatively, several frequencies in a relatively narrow band are used, so that the measurements of one frequency do not override other frequencies. In an exemplary embodiment of the invention, the frequencies 200 Hz, 1000 Hz, and 2000 Hz. Alternatively or additionally, a group of higher frequencies are used. The use of a plurality of frequencies together allows for a more accurate testing of the contact in a short time, since different frequencies may indicate different faults in the contact between the breast and probe 102. Optionally, responsive to the applied wide band frequencies, signals are sensed by each of sensing elements 106. In some embodiments of the invention, signals are also sensed while no signal is applied through electrode 104, for determination of the signal to noise ratio (SNR).

In some embodiments of the invention, the signals used for contact quality determination have at least one characteristic different from signals used for the cancer risk tests. For example, while the signals applied to the patient for contact quality determination include a plurality of frequencies concurrently, in order to save time, the signals applied to the patient for the cancer risk tests are applied each frequency at a separate time in order to maximize the SNR of the tests. Alternatively or additionally, the signals used for the tests have a different amplitude, optionally a higher amplitude, or a higher amplitude per frequency.

Alternatively to applying a signal including all the test frequencies at once, a few signals, each including one or more test frequencies, are applied sequentially through electrode 104. Optionally, in this alternative, the measurements for no applied signal may be taken from the measurements when signals of other frequencies are applied.

Further alternatively, the contact testing is performed at a single frequency, for example the frequency (or one of the frequencies) at which the screening measurements are acquired.

The sensed values of each sensing element 106 are optionally evaluated, for some or all of the frequencies for which measurements were acquired, to determine their signal to noise ratio (SNR). In some embodiments of the invention, measurements are taken while signals are applied to electrode 104 and while no signals (at all or at the applied frequency) are applied to the breast. The SNR is optionally determined as the ratio between the maximum amplitude while signals are applied and while signals are not applied. Alternatively or additionally, the SNR is determined based on average amplitudes. Further alternatively or additionally, the SNR is determined based on a comparison of the signal envelope to the deviation from the envelope. Further alternatively or additionally, the SNR is determined based on a comparison of the signals at the frequencies at which signals were applied to the patient to the average signal values at the frequencies not applied to the patient. The values of the signals at the different frequencies may be determined based on a Fourier transform of the acquired signals. Other known methods of determining SNR can be used.

Alternatively or additionally to testing the contact based on the SNR, the sensed signals are evaluated to determine a resultant impedance value suitable for comparing to predetermined thresholds which define the limits of reasonable values. Further alternatively or additionally, a series of measurements are taken and the evaluation of the contact is based on the stability of the measurements. In some embodiments of the invention, the sensing of the contact testing signals is performed repeatedly for a predetermined number of times (e.g., 10 times) and/or for a predetermined interval, and the sensed values and/or the SNR are tested to verify that they are stable. In an exemplary embodiment of the invention, the reciprocal (1/x) of the standard deviation of the predetermined number of measurements serves as a contact quality indicator.

Alternatively, the contact quality test results are displayed to the operator and the operator is instructed to perform the measurement only when the contact test values were determined to be stable.

Alternatively or additionally, the repeated values are used to provide a more accurate parameter value, for example by averaging over time and/or providing the minimum or maximum. Optionally, the minimal SNR value over time is used in determining the quality level.

Further alternatively or additionally, the contact quality is determined by measuring the pressure of the contact between the sensing elements and the breast surface. Optionally, the sensing elements are mounted on pressure sensing pins that measure the pressure. Alternatively or additionally, one or more pressure sensors are placed on the probe dispersed between the sensing elements. Further alternatively or additionally, any other method is used to measure the pressure and/or to assure that a sufficient pressure is used, for example as described in the above mentioned U.S. patent application Ser. No. 10/033,017.

In some embodiments of the invention, for simplicity, the contact tests are based on only one parameter, such as SNR, measured values being within a suitable range (or above a predetermined value) or stability. Alternatively, the contact-quality test results depend on two or more parameters.

The parameter values from the different frequencies are optionally averaged to provide a combined indication for each of the pixels. Alternatively, a maximal or minimal value is found for one or more of the parameters over the pixels. For example, the quality level may be a function of the minimal SNR of any of the sensing elements. Alternatively or additionally, separate scores are given for different frequencies, for example requiring a suitable SNR for all, or a predetermined number, of the applied frequencies and/or pixels.

In some embodiments of the invention, contact tests are performed for each of the pixels separately. The parameter values of each pixel are optionally compared to a threshold or expected range for the parameter and accordingly an indication on the quality of the contact is provided for the pixel. The indication for each pixel may be a binary indication and/or may be a multi-scale indication. When the contact tests are based on a plurality of parameters, each pixel is optionally given a value that is a weighted average of scores given to each of the parameters. Alternatively, each pixel is given a score that depends on whether each of the parameters has a suitable value.

Optionally, a go ahead signal is provided to the operator of probe 102 when the signals of all the pixels pass the tests (e.g., have values within a given range, have a high SNR, etc.). Alternatively, a multi-scale indication (i.e., on a scale including at least three values), which depends on the number of pixels passing the test, is provided to the operator. In an exemplary embodiment of the invention, the operator is instructed to perform the screening test when at least a predetermined number of pixels have suitable contact values. Optionally, the operator may be allowed the discretion to carry out tests with a lower number of pixels or only with a higher number of pixels. The test results provided by system 100 optionally indicate that a lower number of pixels were used. Optionally, measurements from pixels not passing the contact tests are not used in the screening tests, as described below.

In some embodiments of the invention, the results of the measurements of each of the pixels are displayed to the operator in the form of a map image. Thus, the operator can see where the contact is not suitable and accordingly may adjust the positioning of probe 102 on the breast.

Alternatively to determining a separate score for each pixel, a combined contact-quality score is determined for some or all of the pixels together. Optionally, an average value is determined for a plurality of the pixels, for one or more of the contact-quality parameters. In some embodiments of the invention, a go ahead indication is provided if the average parameter values are within a suitable range. Alternatively or additionally, a multi-level scale display is provided for one or more of the average parameters and/or for a weighted sum of the parameters. In an exemplary embodiment of the invention, a bar with a red, yellow or green value is displayed. For low contact quality, a red display is shown and measurements are prevented by screening system 100. For medium contact quality, a yellow display is shown and the operator may perform a test if a better contact was not achieved although attempts were made. For a green indication, the screening measurements may be taken immediately or even automatically, optionally provided the green indication remains stable.

In some embodiments of the invention, system 100 prevents tests from being performed if the contact quality is not sufficient.

Figure 4:
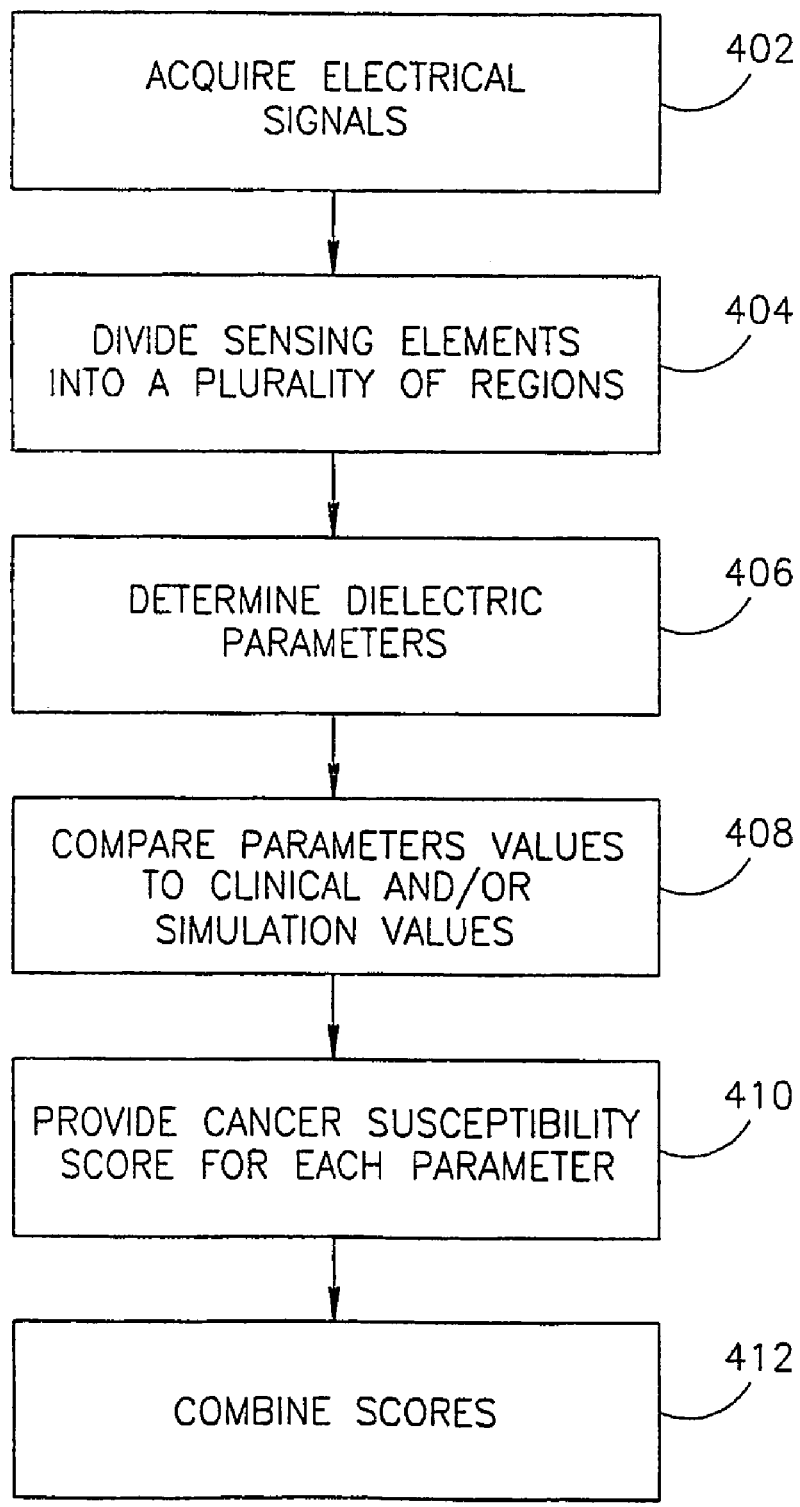
FIG. 4 is a schematic flowchart of acts performed by a breast examination system in determining a breast screening score, in accordance with a first exemplary embodiment of the invention.

FIG. 4 is a schematic flowchart of acts performed by breast examination system 100 in determining a breast screening score, in accordance with a first exemplary embodiment of the invention. In the exemplary embodiment of FIG. 4, all the measurements are optionally taken while probe 102 is placed in a single position on the nipple. In a first stage, electrical measurements are acquired (402) and according to the acquired signals the sensing elements 106 are divided (404) into a plurality of regions, for example an areola region and a surrounding region. Optionally, as described below, each region is handled separately, as the different regions have different dielectric parameter values.

In a second stage, the values of one or more dielectric parameters (examples of which are discussed below) which were found (in clinical tests) to be indicative of breast cancer, are determined (406). The determined parameter values are optionally compared (408) to clinical and/or simulation values, so as to provide (410) a cancer-risk score for each parameter. The cancer-risk scores are then combined (412) so as to provide a total cancer score for the examined breast.

In some embodiments of the invention, the acquiring of the measurements of the first stage and the determination of the dielectric parameter of the second stage are performed responsive to signals applied from electrode 104. In some embodiments of the invention, the applied signals of the first and second stage differ in at least one characteristic for example in frequency and/or amplitude.

The dividing into a plurality of regions optionally differentiates based on one or more external features, i.e., features that are common to substantially all breasts and do not relate to whether the breast is cancerous. Optionally, the different regions are determinable by other means than dielectric characteristics, for example feeling and/or sight, and the differentiation based on impedance is performed for simplicity of the procedure. Optionally, the different regions differ in their surface characteristics. In the following description, an embodiment in which the breast is divided into two types of regions, an areola or nipple region (including both the nipple and the areola) and other breast regions.

In some embodiments of the invention, the signals of the first stage used in dividing (404) the sensing elements into a plurality of regions, optionally comprise low frequency signals (e.g., up to about 1000 Hz, preferably between 200–300 Hz) which better differentiate between the areola and the surrounding skin. At low frequencies, the impedance between breast areas covered skin and the areola which is covered by more delicate skin is relatively high due to the high impedance of skin. Optionally, a real admittance of the underlying flesh is determined from the signals acquired (402) in the first stage. Optionally, the real admittance of all the sensing elements (or all the inner elements as discussed below) is averaged, and the sensing elements having an admittance substantially above the average (e.g., 10–20% above the average) are marked as belonging to the areola.

Thus, the area beneath the sensing elements is divided into two regions, an areola region and a surrounding region. Alternatively to using the real admittance at low frequencies in order to differentiate between the areola region and the surrounding region, any other suitable parameter which varies with the impedance of the skin may be used.

Alternatively or additionally to identifying the areola region according to impedance measurements, the area corresponding to the nipple is determined as an area covered by predetermined pixels corresponding to a marking on surface probe 102, which is placed on the nipple by the physician. In some embodiments of the invention, the area of the nipple is determined based on both the admittance values and the surface probe marking. Further alternatively or additionally, other methods are used to determine the area of the image corresponding to the nipple, for example acquiring an image of the breast with the probe thereon or receiving an indication from the physician.

In some embodiments of the invention, all the pixels not in the areola region are included in the surrounding region. Alternatively, only pixels distanced from the areola region by a predetermined number of pixels (e.g., 1 pixel) are included in the surrounding region. Further alternatively or additionally, the surrounding region includes a same number of pixels as the areola region.

In some embodiments of the invention, measurements are acquired only by the sensing elements which are not on the edges of probe 102, as the values measured by sensing elements 106 at the edges of probe 102 may be affected by cupping effects, which may bias the results. In an exemplary embodiment, probe 102 includes 8×8 sensing elements and the central sensing elements 106 include 6×6 elements. Alternatively or additionally, probe 102 is surrounded by a guard ring held at a ground potential or a reverse potential, so as to reduce cupping effects.

In some embodiments of the invention, the dielectric parameters indicative of breast cancer used in the second stage (after dividing the sensing elements into regions in the first stage) include an imaginary admittance peak frequency of the imaginary admittance. Optionally, the imaginary admittance is determined separately for each sensing element 106 in a plurality of frequencies and the determined imaginary admittance is averaged for each region and frequency. For each region, a frequency close to the peak of the average imaginary admittance is optionally determined. In some embodiments of the invention, one of the frequencies at which the determination of the imaginary admittance was performed, is selected. Optionally, the frequency having the highest average imaginary admittance is assumed to be closest to the peak frequency. Alternatively, an interpolation is performed in order to find a frequency close to the peak point. In some embodiments of the invention, the determination of the peak frequency is performed in a plurality of sub-stages. Optionally, in a first sub-stage, measurements are performed in the expected area of the peak frequency in frequencies separated by relatively large steps, e.g., 1000 Hz.

Generally, the measured imaginary admittance at low frequencies is due to the skin admittance whose imaginary portion increases with the frequency. Between about 1–10 Hz, the imaginary admittance reduces due to a "discharge" of the skin capacitance through the tissue which still has a generally real impedance. The frequency at which this discharge occurs is indicative, in some cases, of the health of the tissue. Generally, the peak frequency is proportional to $G_b/C_s$, where $G_b$ is the admittance of the underlying tissue and $C_s$ is the capacitance of the skin. Therefore, in malignant tissue, the peak frequency is generally at a higher frequency than in healthy tissue.

Optionally, for each region, the peak frequency is determined separately for each pixel of the region and the frequencies are then averaged. Alternatively or additionally, a single peak frequency is determined for all the pixels of the region, by averaging the measured impedance values before determining the imaginary admittance peak frequency.

In an exemplary embodiment of the invention, for the areola region in which the peak frequency is expected to be about 1000-2500 Hz, measurements are acquired at 1000, 2000 and 3000 Hz. In a second sub-stage, measurements are optionally acquired around a frequency determined in the first sub-stage, for example in steps of 100 Hz. Thus, a relatively accurate estimate of the peak frequency may be determined without a very large number of measurements in different frequencies, on the one hand, and without performing an interpolation which may add 'noise' to the calculations. It is noted, that if desired, a third sub-stage may be performed for even more accurate determination of the peak frequency. In the surrounding region, measurements are optionally performed in the frequency range of the expected peak frequency, e.g., between about 3-7 kHz. The phase parameter described below is optionally determined, as mentioned below, at the peak frequency used as this parameter.

As described above, the measurements of the different frequencies are optionally performed separately. Alternatively, the measurements of the different frequencies are performed in parallel, by injecting signals formed of the plurality of tested frequencies.

According to clinical tests, the peak frequency is a relatively good predictor of breast cancer, higher chances of cancer being associated with higher peak frequencies of the imaginary admittance.

Alternatively or additionally to the peak frequency of the imaginary admittance, the dielectric parameters indicative of breast cancer include the impedance phase, which is the phase shift of the measured signal relative to the input, at one or more characteristic frequencies. In some embodiments of the invention, the characteristic frequency at which the phase is determined is the peak frequency of the imaginary admittance. A higher phase is indicative of higher breast cancer chances.

The peak frequency parameter and the phase parameter may be determined for any of one or more of the regions. Each pair of parameter and region is optionally viewed as a separate parameter whose value is compared to a different threshold, and for which a separate risk score is provided.

In determining the parameter value for a region, a value of the parameter is optionally determined separately for each pixel and the values are then averaged. Optionally, only values within a predetermined range of expected values are included in the average. Alternatively or additionally, only a predetermined number of highest, lowest or average values are included in the average. Optionally, if a sufficient number of pixels are not available, the measurements are rejected as if the preliminary contact quality tests did not pass.

Optionally, the values of all the pixels are given the same weight in the average. In some embodiments of the invention, however, the average for the areola region is a weighted average, in which the weight of each pixel depends on the extent to which the pixel belongs to the areola, e.g., the admittance level at 200 Hz. Alternatively or additionally, the weight of each pixel depends on the location of the pixel in the areola region, e.g., whether the pixel is in the center of the region or the side of the region.

Alternatively or additionally to averaging the parameter values of the pixels, the values are combined in any other method which does not include comparing the values of different pixels, for example using an additive function. Further alternatively or additionally, the sensed signals from the different pixels are combined in an additive manner, e.g., averaged, and the value of the dielectric parameter is determined from the combined signal values.

Alternatively or additionally, the dielectric parameters used include other parameters known in the art to be indicative of variations in tissue type, such as the real admittance and/or the variations in the real and/or imaginary impedance.

Further alternatively or additionally, the dielectric parameters indicative of breast cancer include the ratio of the admittance of the surrounding region and the admittance of the areola region at high frequencies (e.g., above 10K Hz, or even above 40-50 kHz).

Figure 5:
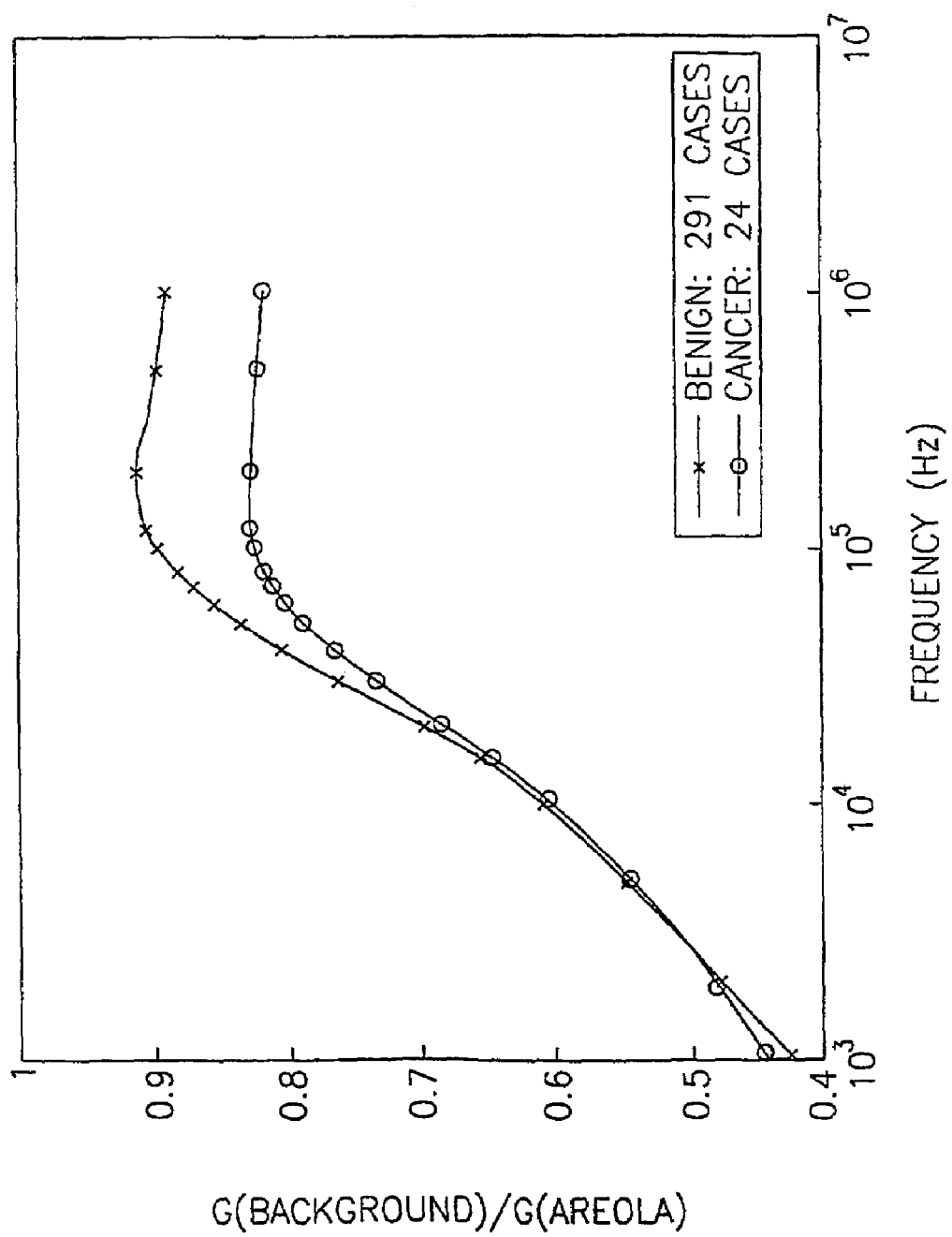
FIG. 5 is a schematic graph of the ratio of background region to areola region admittance as a function of frequency, as determined in clinical tests.

FIG. 5 is a schematic graph of the ratio of background region to areola region admittance as a function of frequency, as determined in clinical tests. As can be seen in FIG. 5, at high frequencies there is a substantial difference in the admittance ratio between healthy and cancerous breasts. Optionally, measurements are performed and the ratio is calculated in a single high frequency. Alternatively, the ratio is calculated for a plurality of high frequencies and the ratios are then averaged. In an exemplary embodiment of the invention, measurements are taken in a plurality of frequencies in the range between 40-150 kHz.

Further alternatively or additionally, the dielectric parameters indicative of breast cancer include the real and/or imaginary admittance in high frequencies.

Figure 6A:
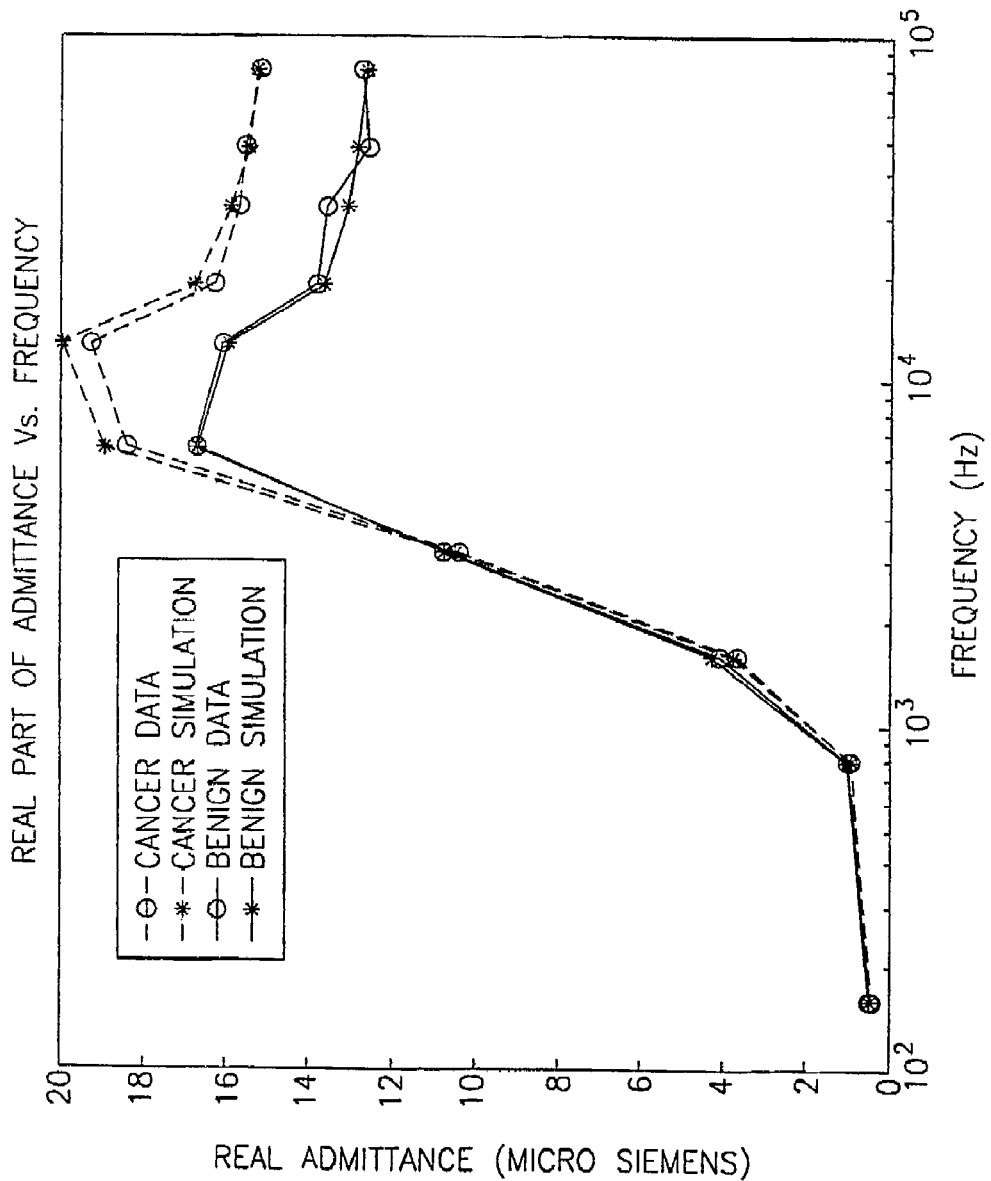
FIG. 6A is a schematic comparative graph of the real part of the admittance of healthy and cancerous breasts, based on simulations and field tests.

FIG. 6A is a schematic comparative graph of the real admittance of healthy and cancerous breasts, based on simulations and field tests. As indicated on the figure, the curves represent the real admittance in field tests for healthy and cancerous breasts, respectively and the real admittance in simulations for healthy and cancerous breasts, respectively. The simulations were performed under the assumption that the breast has a uniform inner tissue impedance and a high impedance value for the skin throughout the breast, except around the nipple, where a lower impedance value is assumed. For healthy breasts, a value of 10 ohm-meter was used in the simulations, while for cancerous breasts a value of 12 ohm/meter was used. The higher impedance is generally due to an increase in the estrogen concentration within the breast and/or to an increase in the blood volume, due to neovascularization.

As can be seen from a comparison of the curves, for frequencies above about 7 kHz, and especially above 50 or even 100 kHz, there is a distinct difference in the real admittance between cancerous and non-cancerous breasts.

Figure 6B:
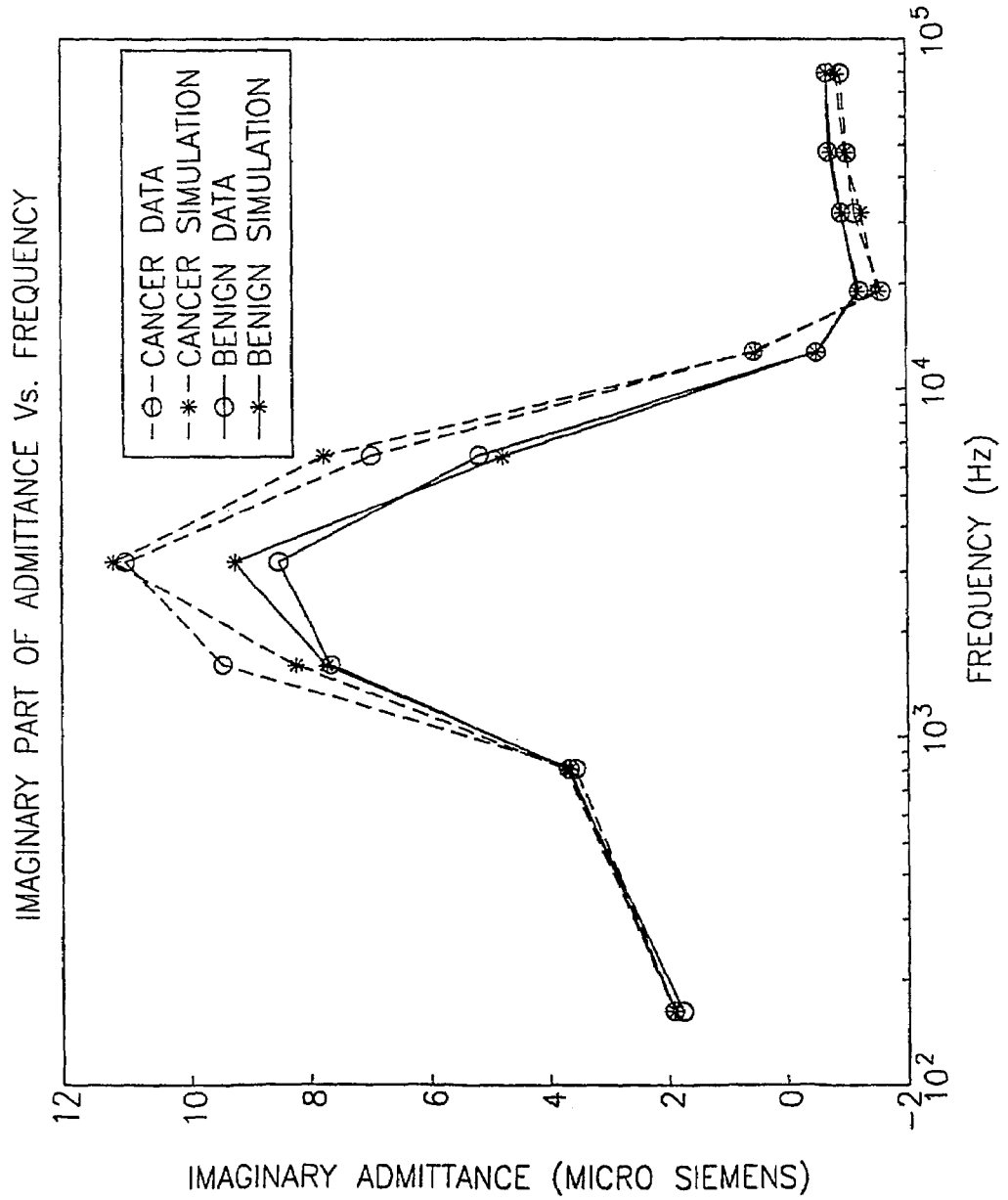
FIG. 6B is a schematic comparative graph of the imaginary part of the admittance of healthy and cancerous breasts, based on simulations and field tests.

FIG. 6B is a schematic comparative graph of the imaginary part of the admittance of healthy and cancerous breasts, based on simulations and field tests. As indicated on the figure, the curves represent the imaginary part of the admittance in field tests for healthy and cancerous breasts, respectively and the imaginary part of the admittance in simulations for healthy and cancerous breasts respectively. As can be seen from FIG. 6B, at frequencies between about 1-10 kHz and especially at about 2-3 kHz, there is a distinct difference between the capacitance of cancerous and non-cancerous breasts.

Optionally, a frequency of about 10-15 kHz is used in determining the real and/or imaginary admittance in high frequencies, as in this frequency band both the real admittance and the capacitance differ for healthy and malignant patients. In some embodiments of the invention, the applied electrical signals and the acquired signals are at a single frequency so as to allow for simple apparatus which is accurately tuned for a single frequency. Alternatively, a frequency in which a highest distinctness of the real admittance is expected, is used. Further alternatively, measurements are acquired for a plurality of suitable frequencies and the dielectric parameters are determined for each of the frequencies separately. The cancer risk score is optionally determined based on an average of the parameter values of the different frequencies. Alternatively, the cancer risk score is determined based on the maximal or minimal value of the parameter over the different frequencies.

As described above, in some embodiments of the invention, in addition to the measurements from the nipple and its surroundings, impedance measurements are acquired from other sectors of the breast. Optionally, from such sectors, measurements are acquired at high frequencies, e.g., above 100 kHz, and are processed as is now described.

In some embodiments of the invention, for each non-nipple sector, a predetermined number of representative pixels (corresponding to sensing elements 106) are selected to represent the sector. The representative pixels are optionally selected as the pixels having a highest admittance at a specific frequency, for example a low frequency. The high admittance is generally indicative of good contact between the sensing elements and the breast. The predetermined number of pixels used is optionally between about 5–15, e.g., 10, thus forming between about 10–20% of the sensing elements. The representative pixels are optionally selected from all the elements of the probe. Alternatively, the representative pixels are selected from the non-edge pixels of the probe 102. For each of the representative pixels, the phase of the impedance is optionally determined, optionally at a peak frequency of the imaginary admittance. The phases of the representative pixels are optionally averaged to receive a sector phase. In some embodiments of the invention, the sector phases of all the sectors measured are averaged to receive a single phase parameter.

Further alternatively or additionally, the same dielectric parameters are determined for both the areola region and the other breast regions. The differentiation between the regions in this embodiment is optionally performed in order to prevent the averaging of the dielectric parameter values and/or signal values from causing loss of data due to the different characteristics of the regions. For example, the imaginary admittance peak frequency generally represents the admittance of the breast tissue relative to the capacitance of the overlaying skin and therefore is different for the nipple and its surroundings. When different parameters are used for the different region types, the differentiation is optionally used to allow choosing the parameters which best differentiate between cancer and healthy tissue for each region. For example, over non-nipple regions higher frequencies generally provide better results than lower frequencies.

Referring in more detail to providing (410) a cancer risk value for each parameter, in some embodiments of the invention, the parameter values are normalized based on clinical test data so that the normalized values all range in a single common range, for example between 0 and 10. Alternatively, the cancer-risk values comprise binary values. Optionally, the cancer risk values are determined according to the number of cancerous cases in a learning group having values above and/or below the parameter values being normalized.

The cancer risk scores are optionally combined (412) by averaging to form the total cancer score. In some embodiments of the invention, a weighted average is used, in which high confidence results are given higher weight. Optionally, predetermined parameters known to have better confidence values are given higher weight in the averaging. Alternatively or additionally, higher weight is given to parameters having lower noise levels and/or clear cut results. Alternatively or additionally, the cancer risk scores of the different regions and/or sub-regions are combined in any other method, optionally a method that does not include the comparison of scores of different regions.

The total cancer score is optionally displayed to the operator of system 100. The operator is optionally instructed to classify the patient as belonging to a high risk group if the total cancer score is above a predetermined level. Alternatively or additionally, the total cancer score is displayed in a graphical manner, for example as a color bar. A green display is optionally shown for very low scores, a yellow display for medium level scores and a red display for high scores that warrant classifying the patient as belonging to a high risk group. It is noted that the classification of a patient as belonging to a high risk group does not necessarily mean that the patient has cancer or even that a lesion was identified in the breast. Rather, the patients in the high risk group have a much higher chance of having cancer than the general population. It is further noted that patients not in the high risk group are not identified as not having cancer. Generally, their chances of having cancer remain at about the level of the entire population. These patients are optionally encouraged to continue with the regular examination procedures they would undergo if they were not examined by system 100.

It is noted that an indication of belonging to the high risk group does not include an indication of a possible location of a cancer tumor. In fact, in some embodiments of the invention, only a limited area of the breast is scanned. The testing in these embodiments is based on the fact that the affect of cancer on the breast is not limited to the area of the lesion and therefore there is no need to see a lesion in order to identify cancer.

The setting of the thresholds used in determining the size of the high risk group and/or the normalization of the parameter values into the risk scores are optionally performed in accordance with a predetermined compromise between sensitivity and specificity. In an exemplary embodiment of the invention, the size of the high risk group is set according to a relatively high specificity, e.g., about 91–95%, even at the cost of a low sensitivity, e.g., about 33–40%. The relatively high specificity is required in order not to send too many healthy patients for further examinations. It is expected that using this specificity, the probability of having a cancer tumor detectable by mammography or any other modality, for women in the high risk group, is about 3–7 times greater than of asymptomatic women.

In some embodiments of the invention, system 100 is used as a first examination unit on breasts not yet examined by other imaging or diagnostic equipment. In an exemplary embodiment of the invention, system 100 is calibrated to send about 5% of the scanned women to additional tests. For these embodiments, it is expected that between 25–50% of the patients with a cancerous breast will be sent for additional tests. These figures can be compared to present clinical breast exams, Ultrasound Examinations and Mammography, which together find 85% of breast cancers. It can thus be used as a stand alone screening procedure for younger women in low risk groups or, preferably, in conjunction with palpation to improve the chances of finding early cancers or pre-cancerous conditions. In general, patients who test positive in the described impedance scan (and/or in the palpation, if performed) would be sent for further testing, as appropriate.

Alternatively to combining the results for the different parameters using a weighted average, any other statistical method of combining parameter values, such as in accordance with Baisean statistics, may be used. Further alternatively, non-parametric methods are used to combine the parameter values such that fewer assumptions on the data are used in forming the breast score. In some embodiments of the invention, in determining whether a patient is to be indicated as belonging to a high risk group, one of the parameters is compared to a threshold, which is set and/or selected according to the value of one or more of the other parameters. The threshold is optionally set according to a desired compromise between specificity and sensitivity as discussed above. Alternatively or additionally, the values of one or more of the other parameters are used to classify the examined patient as belonging to one of a predetermined number of groups. The threshold used is then selected according to the group to which the patient belongs.

In some embodiments of the invention, the classification into groups is based on a value of a dielectric parameter based on measurements from the patient. Optionally, for example for simplicity of the calculations, the parameter used in the group classification does not require generation and/or analysis of an image.

In an exemplary embodiment of the invention, each patient is classified as belonging to one of two groups based on whether the patient has a higher imaginary admittance value at 1000 Hz or at 2000 Hz. The impedance phase at the frequency of the group to which the patient belongs (e.g., 1000 Hz or 2000 Hz) is compared to a threshold selected according to clinical data of patients belonging to the group to which the examined patient belongs. For each group, a threshold is optionally selected according to available clinical data of patients belonging to the group, in order to meet a desired specificity and/or sensitivity.

Optionally, the threshold of the group is also adjusted according to a measure of the quality of the contact, such as the size of the hole in the high admittance region around the nipple, if such a hole exists.

In some embodiments of the invention, additional groups are defined, for example according to non-dielectric information on the patient, such as age, hormonal state of the patient, time of day, the time in the menstrual period of the patient, the size of the breast and/or the nipple and/or other physical characteristics of the patient. Alternatively or additionally to defining different groups and handling the clinical data of each group separately, the threshold of some or all of the groups are adjusted according to the non-dielectric information. For example, as cancer risk increases with age, the threshold for indicating high risk may be lowered as the age of the patient is greater.

In some embodiments of the invention, instead of configuring system 100 with thresholds based on clinical data held by a producer of system 100, system 100 is configured with the clinical data and indicated a tested patient as belonging to a high risk group based on the number of clinical data cases having higher and/or lower values than the value of the parameter in the tested patient.

In some embodiments of the invention, system 100 allows an operator to set the specificity of the system. For example, when system 100 is used on young women in a gynecologist's clinic, system 100 is set to operate with a relatively high specificity, so as to limit the number of women sent unnecessarily for further tests. Alternatively, system 100 is set to a relatively high sensitivity in order to encourage women to go for further testing. The physician operating system 100 may select the specificity/sensitivity working point according to the expected behavior of the patients of the physician. Optionally, for older women and/or women who already underwent further tests, a higher sensitivity is used.

It is noted that the order of the tests and calculations described above is brought as an example, and that the tests may be carried out in a different order. For example, all the measurements required for the selected frequency may be performed for each frequency before the selection of the peak frequency or may be performed only after the selection of the peak frequency.

Figure 7:
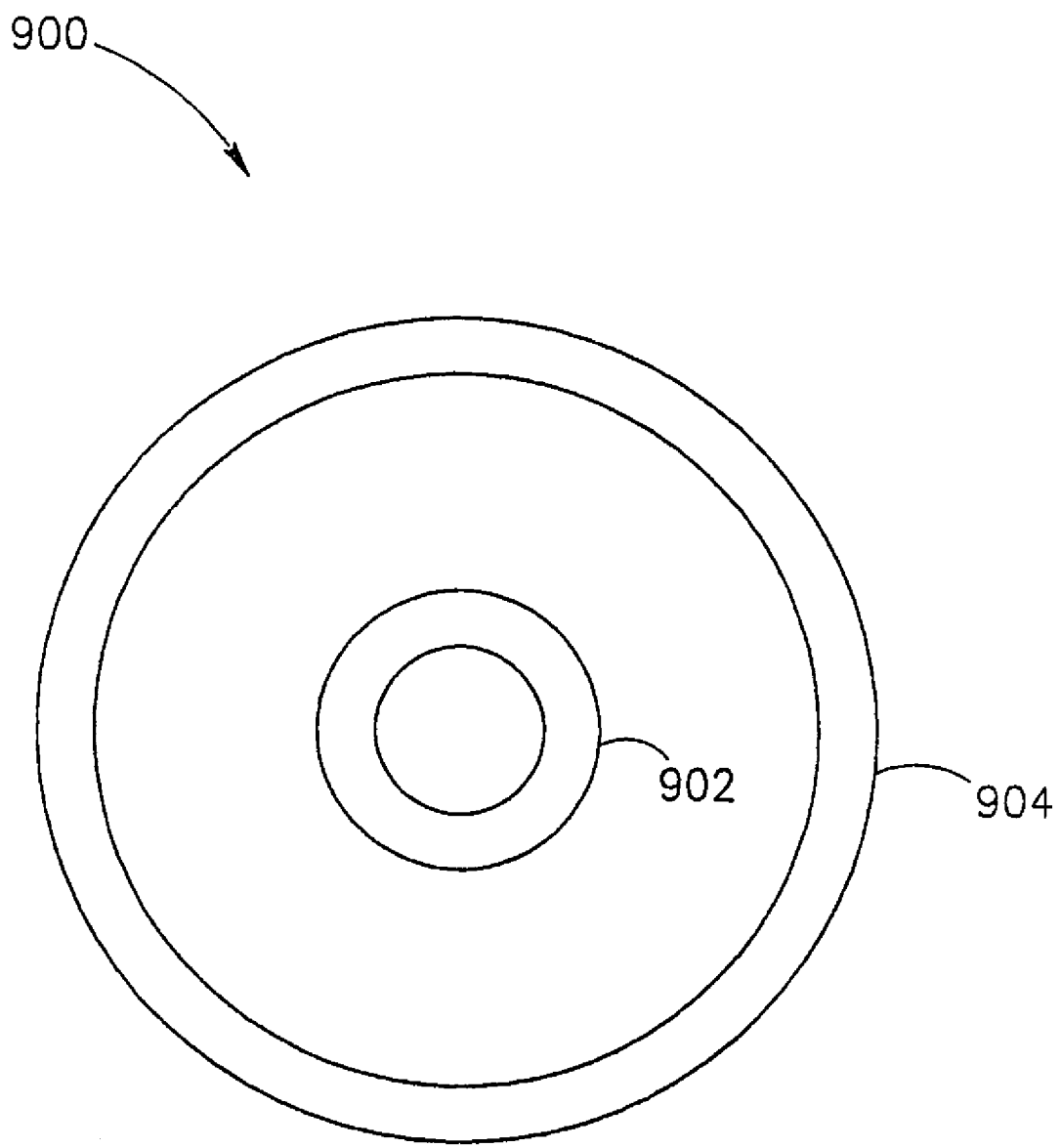
FIG. 7 is a bottom view of a breast examination probe, in accordance with an exemplary embodiment of the invention.

FIG. 7 is a schematic bottom view of a breast examination probe 900, in accordance with an exemplary embodiment of the invention. Probe 900 comprises two substantially concentric rings 902 and 904 which serve as electrodes. Optionally, ring 902 has a small diameter, such that small ring 902 collects signals from the areola. Large ring 904 optionally has a larger diameter such that it collects signals from the breast area beyond the areola.

In some embodiments of the invention, rings 902 and 904 have the same total sensing area. Alternatively or additionally, the system compensates for the difference in sensing area when necessary. Optionally, smaller ring 902 is thicker so that the contact areas of the rings with the breast are substantially the same. Alternatively or additionally, some portions of one or both of the rings are covered with an isolating material so as to equalize the contact area with the breast, or otherwise limit the contact area of one or more of the rings.

In some embodiments of the invention, rings 902 and/or 904 are segmented into a plurality of separate electrodes, such that the contact quality of each segment can be determined separately, thus enhancing the accuracy of the impedance test procedure as discussed above.

In some embodiments of the invention, probe 900 includes additional concentric rings. For example, a plurality of closely spaced inner rings may be used to sense signals from the areola region, for example to determine an impedance map of the areola. Alternatively or additionally, a large outer ring may be used as a source electrode (corresponding to source electrode 104 of FIG. 1) or a voltage measurement electrode (corresponding to electrode 108 of FIG. 1). Further alternatively or additionally, probe 900 may include only a single ring used for sensing signals from the areola.

Although the methods of the above description relate to identifying breast cancer, some of the methods may be adapted with required changes to identification of other cancers or disease states identifiable based on impedance differences. It is noted, however, that breast cancer is different from other cancers (e.g., cervix and skin cancer) in that the malignant tissue is not close to or on a surface accessible by a probe (without invasive surgery).

It will be appreciated that the above-described methods may be varied in many ways, including, changing the order of steps, and/or performing a plurality of steps concurrently. For example, surface probe 102 is not limited to any specific shape. In some embodiments of the invention, surface probe 102 may have a circular shape, so as to minimize the extent of the perimeter of the probe relative to its surface area. Alternatively, surface probe 102 has a polygon shape, triangular shape and/or a rectangular shape. It should also be appreciated that the above described description of methods and apparatus are to be interpreted as including apparatus for carrying out the methods, and methods of using the apparatus.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features, and/or steps shown in a particular figure or described with respect to one of the embodiments. Variations of embodiments described will occur to persons of the art. Furthermore, the terms "comprise," "include," "have" and their conjugates, shall mean, when used in the claims, "including but not necessarily limited to."

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims.

What is claimed is:

1. A method of screening for breast cancer, comprising:
testing a plurality of asymptomatic women by measuring at least one electrical impedance characteristic on at least one breast, said asymptomatic woman being classified as belonging to a first group having a first risk factor for breast cancer; and
re-classifying some of the women as belonging to a second group having a second risk factor greater than the first risk factor, based on the at least one impedance characteristic,
wherein the second group has a risk factor of at least twice that of the first group, but less than 15 times that of the first group; and
wherein fewer than 50% of those in the first group that have breast cancer are reclassified into the second group.

2. A method according to claim 1, wherein the second group has a risk factor at least 5 times as high as that of the first group.

3. A method according to claim 1, wherein the second group has a risk factor at least 10 times as high as that of the first group.

4. A method according to claim 1 wherein the first group consists of a general population of women between 15 and 40 years old.

5. A method according to claim 4 wherein the first group consists of a general population of women between 20 and 35 years old.

6. A method according to claim 1 wherein more than 20% percent of women having cancer in the first group are re-classified in said second group.

7. A method according to claim 6 wherein more than 25% percent of women having cancer in the first group are re-classified in said second group.

8. A method according to claim 6 wherein more than 30% percent of women having cancer in the first group are re-classified in said second group.

9. A method according to claim 6, wherein fewer than 40% of women having cancer in the first group are re-classified in said second group.

10. A method according to claim 7, wherein fewer than 40% of women having cancer in the first group are re-classified in said second group.

11. A method according to claim 8, wherein fewer than 40% of women having cancer in the first group are re-classified in said second group.

12. A method according to claim 1, wherein up to 10% of the women in the first group not having cancer are placed in the second group.

13. A method according to claim 1 wherein between 5% and 10% of the woman in the first group, not having cancer are placed in the second group.

14. Apparatus for breast cancer screening, comprising:
a probe for acquiring electrical signals from a breast of a patient, belonging to a low risk group for breast cancer, having a first risk factor for having breast cancer; and
a processor adapted to determine at least one dielectric parameter value responsive to signals acquired by the probe and to classify the patient as to whether she belongs to a high risk group, having a second risk factor of having breast cancer greater than the first risk factor, based on the at least one dielectric parameter,
wherein the processor is calibrated to classify less than 50% of women having cancer detectable by mammography in the low risk group as belonging to the high risk group and wherein the high risk group has a risk factor of at least twice that of the low risk group, but less than 15 times that of the low risk group.

15. Apparatus according to claim 14, wherein the processor is calibrated to classify less than 45% of women having cancer detectable by mammography in the low risk group as belonging to the high risk group.

16. Apparatus according to claim 14, wherein the processor is calibrated to classify less than 40% of women having cancer detectable by mammography in the low risk group as belonging to the high risk group.

17. Apparatus according to claim 14, wherein the processor is calibrated to classify less than 35% of women having cancer detectable by mammography in the low risk group as belonging to the high risk group.

18. Apparatus according to claim 14, wherein the processor is calibrated to classify less than 10% of the women in the low risk group as belonging to the high risk group.

19. A method of screening for breast cancer, comprising:
testing a plurality of asymptomatic women by measuring at least one electrical impedance characteristic on at least one breast, said asymptomatic woman being classified as belonging to a first group having a first risk factor for breast cancer; and
re-classifying some of the women as belonging to a second group having a second risk factor greater than the first risk factor, based on the at least one impedance characteristic,
wherein fewer than 10% of the women in the first group are reclassified into the second group.

20. A method according to claim 19, wherein fewer than 50% of the women in the first group that have cancer are reclassified into the second group.

* * * * *